(12) United States Patent
Blatt et al.

(10) Patent No.: US 10,010,536 B2
(45) Date of Patent: Jul. 3, 2018

(54) METHOD OF MODULATING STRESS-ACTIVATED PROTEIN KINASE SYSTEM

(71) Applicant: InterMune, Inc., South San Francisco, CA (US)

(72) Inventors: Lawrence M. Blatt, Healdsburg, CA (US); Scott D. Seiwert, Seattle, WA (US); Leonid D. Beigelman, San Mateo, CA (US); Ramachandran Radhakrishnan, Fremont, CA (US); Karl Kossen, Brisbane, CA (US); Vladimir Serebryany, Burlingame, CA (US)

(73) Assignee: INTERMUNE, INC., Brisbane, CA (US)

(*) Notice: Subject to any disclaimer, the term of this patent is extended or adjusted under 35 U.S.C. 154(b) by 0 days.

(21) Appl. No.: 15/387,537

(22) Filed: Dec. 21, 2016

(65) Prior Publication Data

US 2017/0095462 A1 Apr. 6, 2017

Related U.S. Application Data

(60) Division of application No. 14/263,787, filed on Apr. 28, 2014, now Pat. No. 9,527,816, which is a continuation of application No. 13/528,624, filed on Jun. 20, 2012, now Pat. No. 8,741,936, which is a continuation of application No. 12/790,099, filed on May 28, 2010, now abandoned, which is a division of application No. 11/431,132, filed on May 9, 2006, now Pat. No. 7,728,013.

(60) Provisional application No. 60/679,471, filed on May 10, 2005, provisional application No. 60/732,230, filed on Nov. 1, 2005.

(51) Int. Cl.
*A61K 31/4412* (2006.01)
*A61K 31/44* (2006.01)
*A61K 31/444* (2006.01)

(52) U.S. Cl.
CPC .......... *A61K 31/4412* (2013.01); *A61K 31/44* (2013.01); *A61K 31/444* (2013.01)

(58) Field of Classification Search
CPC ................................................. A61K 31/4412
See application file for complete search history.

(56) References Cited

U.S. PATENT DOCUMENTS

| | | | |
|---|---|---|---|
| 3,014,034 A | 12/1961 | Druey et al. | |
| 3,622,340 A | 11/1971 | Lamon | |
| 3,839,346 A | 10/1974 | Gadekar et al. | |
| 3,974,281 A | 8/1976 | Gadekar | |
| 4,042,699 A | 8/1977 | Gadekar | |
| 4,052,509 A | 10/1977 | Gadekar | |
| 4,256,640 A | 3/1981 | Makisumi et al. | |
| 4,258,052 A | 3/1981 | Yu et al. | |
| 4,325,863 A | 4/1982 | Hinsken et al. | |
| 4,397,854 A | 8/1983 | Sircar | |
| 4,404,203 A | 9/1983 | Sircar | |
| 4,473,696 A | 9/1984 | Hartmann et al. | |
| 4,576,942 A | 3/1986 | Youssefyeh | |
| 4,645,839 A | 2/1987 | Kruse et al. | |
| 4,650,804 A | 3/1987 | Kitaura et al. | |
| 4,698,349 A | 10/1987 | Kitaura et al. | |
| 4,820,309 A | 4/1989 | Holliger | |
| 4,898,654 A | 2/1990 | Toda et al. | |
| 5,019,365 A | 5/1991 | Bedell | |
| 5,077,142 A | 12/1991 | Sakon et al. | |
| 5,080,710 A | 1/1992 | Rueb et al. | |
| 5,167,941 A | 12/1992 | Bedell et al. | |
| 5,241,065 A | 8/1993 | Berger et al. | |
| 5,310,562 A | 5/1994 | Margolin | |
| 5,356,904 A | 10/1994 | Freidinger et al. | |
| 5,466,697 A | 1/1995 | Wilhelm et al. | |
| 5,401,738 A | 3/1995 | Mederski et al. | |
| 5,457,099 A | 10/1995 | Shogaki et al. | |
| 5,518,729 A | 5/1996 | Margolin | |
| 5,543,521 A | 8/1996 | Chan et al. | |
| 5,552,409 A | 9/1996 | Michelotti et al. | |
| 5,716,632 A | 2/1998 | Margolin | |
| 5,719,155 A | 2/1998 | Cho et al. | |
| 5,731,106 A | 3/1998 | Tsutsumi et al. | |
| 5,741,793 A | 4/1998 | Young et al. | |

(Continued)

FOREIGN PATENT DOCUMENTS

| | | |
|---|---|---|
| AT | 333774 B | 12/1976 |
| CA | 1085857 A | 9/1980 |

(Continued)

OTHER PUBLICATIONS

Ammar et al., Novel Pirfenidone Analogues: Synthesis of Pyridin-2-ones for the Treatment of Pulmonary Fibrosis, Arch Pharm Chem Life Sci., (Apr. 2006) 339(8): 429-426.

(Continued)

*Primary Examiner* — Samira Jean-Louis

(74) *Attorney, Agent, or Firm* — Marshall, Gerstein & Borun LLP

(57) ABSTRACT

Disclosed are methods of modulating a stress activated protein kinase (SAPK) system with an active compound, wherein the active compound exhibits low potency for inhibition of at least one p38 MAPK; and wherein the contacting is conducted at a SAPK-modulating concentration that is at a low percentage inhibitory concentration for inhibition of the at least one p38 MAPK by the compound. Also disclosed are derivatives of pirfenidone. These derivatives can modulate a stress activated protein kinase (SAPK) system.

4 Claims, 7 Drawing Sheets

(56) References Cited

U.S. PATENT DOCUMENTS

| | | |
|---|---|---|
| 5,808,015 A | 9/1998 | Hamprecht |
| 5,817,700 A | 10/1998 | Dube et al. |
| 5,859,041 A | 1/1999 | Liverton et al. |
| 5,962,478 A | 10/1999 | Margolin |
| 6,090,822 A | 7/2000 | Margolin |
| 6,114,353 A | 9/2000 | Margolin |
| 6,117,973 A | 9/2000 | Batz et al. |
| 6,174,901 B1 | 1/2001 | Mantlo et al. |
| 6,225,052 B1 | 5/2001 | Batz et al. |
| 6,265,350 B1 | 7/2001 | Schnatterer et al. |
| 6,300,349 B1 | 10/2001 | Margolin |
| 6,307,047 B1 | 10/2001 | Black et al. |
| 6,509,354 B1 | 1/2003 | Toriyabe et al. |
| 6,521,656 B1 | 2/2003 | Kaneko et al. |
| 6,551,963 B1 | 4/2003 | Linker et al. |
| 6,586,447 B1 | 7/2003 | Lyssikatos et al. |
| 6,602,826 B1 | 8/2003 | Andree et al. |
| 6,750,232 B2 | 6/2004 | Harada et al. |
| 6,949,571 B2 | 9/2005 | Nagato et al. |
| 7,067,540 B2 | 6/2006 | Devadas et al. |
| 7,728,013 B2 | 6/2010 | Blatt et al. |
| 7,939,549 B2 | 5/2011 | Nagato et al. |
| 8,741,936 B2 | 6/2014 | Blatt et al. |
| 2002/0077486 A1 | 6/2002 | Scarborough et al. |
| 2003/0065175 A1 | 4/2003 | Natsan et al. |
| 2003/0162130 A1 | 8/2003 | Murota |
| 2003/0194748 A1 | 10/2003 | Nagasaki |
| 2003/0199692 A1 | 10/2003 | Biediger et al. |
| 2003/0220368 A1 | 11/2003 | Ozaki et al. |
| 2004/0006082 A1 | 1/2004 | Harada et al. |
| 2004/0014986 A1 | 1/2004 | Hendel et al. |
| 2004/0023973 A1 | 2/2004 | Nagato et al. |
| 2004/0048902 A1 | 3/2004 | Kiyonaka et al. |
| 2004/0058964 A1 | 3/2004 | Devadas et al. |
| 2004/0063955 A1 | 4/2004 | Biediger et al. |
| 2004/0082619 A1 | 4/2004 | Tada et al. |
| 2004/0097560 A1 | 5/2004 | Warshakoon et al. |
| 2004/0102494 A1 | 5/2004 | Selvakumar et al. |
| 2004/0142950 A1 | 7/2004 | Bunker et al. |
| 2004/0157738 A1 | 8/2004 | Tsukamoto et al. |
| 2004/0180906 A1 | 9/2004 | Flynn et al. |
| 2004/0235886 A1 | 11/2004 | Charifson et al. |
| 2004/0259864 A1 | 12/2004 | Geneste et al. |
| 2004/0259865 A1 | 12/2004 | Harada et al. |
| 2005/0004149 A1 | 1/2005 | Harada et al. |
| 2005/0020594 A1 | 1/2005 | Hepperle et al. |
| 2005/0038247 A1 | 2/2005 | Charifson et al. |
| 2005/0054631 A1 | 3/2005 | Jiang et al. |
| 2005/0065144 A1 | 3/2005 | Feng et al. |
| 2005/0101590 A1 | 5/2005 | Yasui et al. |
| 2005/0130943 A1 | 6/2005 | Wallace et al. |
| 2005/0130976 A1 | 6/2005 | Wallace et al. |
| 2005/0153941 A1 | 7/2005 | Miyabayashi et al. |
| 2005/0153942 A1 | 7/2005 | Wallace et al. |
| 2005/0176775 A1 | 8/2005 | Devadas et al. |
| 2005/0245581 A1 | 11/2005 | Nagato et al. |
| 2005/0250782 A1 | 11/2005 | Marlow et al. |
| 2005/0256123 A1 | 11/2005 | Marlow et al. |
| 2005/0256136 A1 | 11/2005 | Charifson et al. |
| 2005/0288286 A1 | 12/2005 | Flynn et al. |
| 2006/0025337 A1 | 2/2006 | Sinclair et al. |
| 2006/0025424 A1 | 2/2006 | Charifson et al. |
| 2006/0069260 A1 | 3/2006 | Zhang et al. |
| 2006/0084135 A1 | 4/2006 | Howitz et al. |
| 2006/0100193 A1 | 5/2006 | Zhu et al. |
| 2006/0111355 A1 | 5/2006 | Garrick et al. |
| 2006/0160862 A1 | 7/2006 | Charrier et al. |
| 2006/0189616 A1 | 8/2006 | Pelletier et al. |
| 2006/0189617 A1 | 8/2006 | Pelletier et al. |
| 2006/0211577 A1 | 9/2006 | Hamprecht et al. |
| 2006/0287319 A1 | 12/2006 | Jiang et al. |
| 2007/0037808 A1 | 2/2007 | Flynn et al. |
| 2007/0037822 A1 | 2/2007 | Letourneau et al. |
| 2007/0037973 A1 | 2/2007 | Momiyama et al. |
| 2007/0049624 A1 | 3/2007 | Yi |
| 2007/0105890 A1 | 5/2007 | Nakahira et al. |
| 2007/0112038 A1 | 5/2007 | Marlow et al. |
| 2007/0142640 A1 | 6/2007 | Arimoto et al. |
| 2007/0149513 A1 | 6/2007 | Chen et al. |
| 2007/0179165 A1 | 8/2007 | Gyorkos et al. |
| 2007/0185092 A1 | 8/2007 | Zhu et al. |
| 2007/0191336 A1 | 8/2007 | Flynn et al. |
| 2007/0219182 A1 | 9/2007 | Lubisch et al. |
| 2007/0259924 A1 | 11/2007 | Song et al. |
| 2008/0081825 A1 | 4/2008 | Nakai et al. |
| 2008/0103139 A1 | 5/2008 | Ishizuka et al. |
| 2009/0318455 A1 | 12/2009 | Kossen et al. |
| 2010/0240704 A1 | 9/2010 | Blatt et al. |
| 2011/0034495 A1 | 2/2011 | Seiwert et al. |
| 2012/0015984 A1 | 1/2012 | Radhakrishnan et al. |
| 2012/0046321 A1 | 2/2012 | Olgin et al. |
| 2012/0258924 A1 | 10/2012 | Blatt et al. |

FOREIGN PATENT DOCUMENTS

| | | |
|---|---|---|
| CA | 26037363 A1 | 10/2006 |
| CH | 312530 A | 12/1955 |
| CH | 312531 A | 12/1955 |
| CH | 333366 | 10/1958 |
| CN | 1349982 | 5/2002 |
| CN | 1386737 | 12/2002 |
| CN | 1417209 | 5/2003 |
| CN | 1676518 A | 10/2005 |
| DE | 1070639 | 4/1964 |
| DE | 1936231 | 10/1970 |
| DE | 2557342 A1 | 6/1977 |
| DE | 2707268 A1 | 8/1978 |
| DE | 2830700 | 2/1979 |
| DE | 149666 A1 | 7/1981 |
| DE | 4423934 A1 | 3/1995 |
| DE | 19754348 A1 | 6/1998 |
| DE | 19821263 A1 | 11/1998 |
| DE | 19726241 A1 | 12/1998 |
| DE | 19729061 | 1/1999 |
| DE | 19918725 A1 | 10/2000 |
| DE | 10024938 | 11/2001 |
| DE | 10345648 A1 | 4/2005 |
| EA | 0648760 A2 | 4/1995 |
| EP | 0104860 A1 | 4/1984 |
| EP | 0241006 A2 | 10/1987 |
| EP | 0259048 A2 | 3/1988 |
| EP | 0311010 A2 | 4/1989 |
| EP | 0319957 A2 | 6/1989 |
| EP | 0381374 A1 | 8/1990 |
| EP | 0393936 A1 | 10/1990 |
| EP | 0409435 A1 | 1/1991 |
| EP | 0478195 A1 | 4/1992 |
| EP | 0531578 A1 | 3/1993 |
| EP | 0548680 A1 | 6/1993 |
| EP | 0577325 A1 | 1/1994 |
| EP | 0579059 A1 | 1/1994 |
| EP | 0602515 A1 | 6/1994 |
| EP | 0626377 A1 | 11/1994 |
| EP | 0733629 A1 | 9/1996 |
| EP | 0733716 A2 | 10/1996 |
| EP | 0760208 A2 | 3/1997 |
| EP | 0835865 A1 | 4/1998 |
| EP | 0856255 A2 | 8/1998 |
| EP | 1186318 A2 | 3/2002 |
| EP | 1213288 A1 | 6/2002 |
| EP | 1400243 A1 | 3/2004 |
| FR | 2046068 A5 | 3/1971 |
| FR | 2774986 A1 | 8/1999 |
| FR | 2797629 A1 | 2/2001 |
| GB | 0788393 | 1/1958 |
| GB | 0889317 | 2/1962 |
| GB | 1388001 A | 3/1975 |
| GB | 1458048 A | 12/1976 |
| GB | 1458049 A | 12/1976 |
| GB | 1596887 A | 9/1981 |
| JP | 42002264 | 2/1967 |
| JP | 51128438 A | 11/1976 |
| JP | 57021388 A | 2/1982 |
| JP | 57077671 A | 5/1982 |

(56) References Cited

FOREIGN PATENT DOCUMENTS

| | | |
|---|---|---|
| JP | 63290821 A | 11/1988 |
| JP | 3043744 A | 2/1991 |
| JP | 4223457 A | 8/1992 |
| JP | 6256187 A | 9/1994 |
| JP | 7128793 A | 5/1995 |
| JP | 7233072 A | 9/1995 |
| JP | 7295165 A | 11/1995 |
| JP | 7295166 A | 11/1995 |
| JP | 8134371 A | 5/1996 |
| JP | H 08-510251 | 10/1996 |
| JP | 9244235 A | 9/1997 |
| JP | 9249567 A | 9/1997 |
| JP | 9319023 A | 12/1997 |
| JP | 11049755 A | 2/1999 |
| JP | H 11-501911 | 2/1999 |
| JP | 1180952 A | 7/1999 |
| JP | 11-512699 | 11/1999 |
| JP | 2002371078 A | 12/2002 |
| JP | 2003012645 A | 1/2003 |
| JP | 2003238611 A | 8/2003 |
| JP | 2003261535 A | 9/2003 |
| JP | 2004269469 A | 9/2004 |
| JP | 2004315594 A | 11/2004 |
| JP | 2004359641 | 12/2004 |
| JP | 2005013152 A | 1/2005 |
| JP | 2005145882 A | 6/2005 |
| JP | 2005-526068 | 9/2005 |
| JP | 2005255675 A | 9/2005 |
| JP | 2006-5179676 | 8/2006 |
| KR | 10-2000-0010676 | 2/2000 |
| WO | WO 1991/14674 | 10/1991 |
| WO | WO 1992/13451 | 8/1992 |
| WO | WO 1992/20642 | 11/1992 |
| WO | WO 1992/20816 | 11/1992 |
| WO | WO 1993/21185 | 10/1993 |
| WO | WO 1993/23404 | 11/1993 |
| WO | WO 1994/17059 | 8/1994 |
| WO | WO 1994/26249 | 11/1994 |
| WO | WO 1995/16712 | 6/1995 |
| WO | WO 1995/18128 | 7/1995 |
| WO | WO 1996/18770 | 6/1996 |
| WO | WO 1996/27374 | 9/1996 |
| WO | WO 1996/33994 | 10/1996 |
| WO | WO 1997/05109 | 2/1997 |
| WO | WO 1997/05137 | 2/1997 |
| WO | WO 1997/10712 | 3/1997 |
| WO | WO 1997/29107 | 8/1997 |
| WO | WO 1997/36863 | 10/1997 |
| WO | WO 1997/41830 | 11/1997 |
| WO | WO 1998/13361 | 4/1998 |
| WO | WO 1998/29119 | 7/1998 |
| WO | WO 1998/51772 | 11/1998 |
| WO | WO 1998/52948 | 11/1998 |
| WO | WO 1999/02501 | 1/1999 |
| WO | WO 1999/05123 | 2/1999 |
| WO | WO 1999/05125 | 2/1999 |
| WO | WO 1999/05913 | 2/1999 |
| WO | WO 1999/10331 | 3/1999 |
| WO | WO 1999/10332 | 3/1999 |
| WO | WO 1999/12903 | 3/1999 |
| WO | WO 1999/21837 | 5/1999 |
| WO | WO 1999/26944 | 6/1999 |
| WO | WO 1999/28313 | 6/1999 |
| WO | WO 1999/32448 | 7/1999 |
| WO | WO 1999/38857 | 8/1999 |
| WO | WO 1999/47140 | 9/1999 |
| WO | WO 1999/50263 | 10/1999 |
| WO | WO 1999/52878 | 10/1999 |
| WO | WO 1999/55676 | 11/1999 |
| WO | WO 1999/62900 | 12/1999 |
| WO | WO 2000/016775 | 3/2000 |
| WO | WO 2000/025789 | 5/2000 |
| WO | WO 2000/044381 | 8/2000 |
| WO | WO 2000/068188 | 11/2000 |
| WO | WO 2001/012600 | 2/2001 |
| WO | WO 2001/056992 | 8/2001 |
| WO | WO 2001/057019 | 8/2001 |
| WO | WO 2001/057021 | 8/2001 |
| WO | WO 2001/057037 | 8/2001 |
| WO | WO 2001/058448 | 8/2001 |
| WO | WO 2001/062253 | 8/2001 |
| WO | WO 2001/070746 | 9/2001 |
| WO | WO 2001/072708 | 10/2001 |
| WO | WO 2001/096308 | 12/2001 |
| WO | WO 2002/006244 | 1/2002 |
| WO | WO 2002/022587 | 3/2002 |
| WO | WO 2002/024650 | 3/2002 |
| WO | WO 2002/040448 | 5/2002 |
| WO | WO 2002/060446 | 8/2002 |
| WO | WO 2002/067675 | 9/2002 |
| WO | WO 2002/085858 | 10/2002 |
| WO | WO 2002/090334 | 11/2002 |
| WO | WO 2002/098853 | 12/2002 |
| WO | WO 2003/014087 | 2/2003 |
| WO | WO 2003/033502 | 4/2003 |
| WO | WO 2003/035650 | 5/2003 |
| WO | WO 2003/045912 | 6/2003 |
| WO | WO 2003/047347 | 6/2003 |
| WO | WO 2003/047577 | 6/2003 |
| WO | WO 2003/059871 | 7/2003 |
| WO | WO 2003/059891 | 7/2003 |
| WO | WO 2003/068230 | 8/2003 |
| WO | WO 2003/076405 | 9/2003 |
| WO | WO 2003/082265 | 10/2003 |
| WO | WO 2003/093273 | 11/2003 |
| WO | WO 2003/097062 | 11/2003 |
| WO | WO 2003/106452 | 12/2003 |
| WO | WO 2004/000355 | 12/2003 |
| WO | WO 2004/000846 | 12/2003 |
| WO | WO 2004/005286 | 1/2004 |
| WO | WO 2004/006906 | 1/2004 |
| WO | WO 2004/009560 | 1/2004 |
| WO | WO 2004/014859 | 2/2004 |
| WO | WO 2004/014892 | 2/2004 |
| WO | WO 2004/019863 | 3/2004 |
| WO | WO 2004/024078 | 3/2004 |
| WO | WO 2004/024152 | 3/2004 |
| WO | WO 2004/031145 | 4/2004 |
| WO | WO 2004/031188 | 4/2004 |
| WO | WO 2004/037159 | 5/2004 |
| WO | WO 2004/048314 | 6/2004 |
| WO | WO 2004/058256 | 7/2004 |
| WO | WO 2004/060306 | 7/2004 |
| WO | WO 2004/072033 | 8/2004 |
| WO | WO 2004/073628 | 9/2004 |
| WO | WO 2004/074282 | 9/2004 |
| WO | WO 2004/078174 | 9/2004 |
| WO | WO 2004/103296 | 12/2004 |
| WO | WO 2004/105684 | 12/2004 |
| WO | WO 2004/110245 | 12/2004 |
| WO | WO 2004/113347 | 12/2004 |
| WO | WO 2005/000227 | 1/2005 |
| WO | WO 2005/000818 | 1/2005 |
| WO | WO 2005/002672 | 1/2005 |
| WO | WO 2005/007632 | 1/2005 |
| WO | WO 2005/012288 | 2/2005 |
| WO | WO 2005/013917 | 2/2005 |
| WO | WO 2005/018557 | 3/2005 |
| WO | WO 2005/026123 | 3/2005 |
| WO | WO 2005/026124 | 3/2005 |
| WO | WO 2005/039598 | 5/2005 |
| WO | WO 2005/040758 | 5/2005 |
| WO | WO 2005/053707 | 6/2005 |
| WO | WO 2005/073222 | 8/2005 |
| WO | WO 2005/075438 | 8/2005 |
| WO | WO 2005/085200 | 9/2005 |
| WO | WO 2005/090294 | 9/2005 |
| WO | WO 2005/096784 | 10/2005 |
| WO | WO 2005/097750 | 10/2005 |
| WO | WO 2005/099688 | 10/2005 |
| WO | WO 2005/105743 | 11/2005 |
| WO | WO 2005/105790 | 11/2005 |
| WO | WO 2006/004107 | 1/2006 |
| WO | WO 2006/011024 | 2/2006 |

(56) References Cited

FOREIGN PATENT DOCUMENTS

| | | |
|---|---|---|
| WO | WO 2006/017443 | 2/2006 |
| WO | WO 2006/020145 | 2/2006 |
| WO | WO 2006/026305 | 3/2006 |
| WO | WO 2006/030032 | 3/2006 |
| WO | WO 2006/032631 | 3/2006 |
| WO | WO 2006/038734 | 4/2006 |
| WO | WO 2006/044405 | 4/2006 |
| WO | WO 2006/046778 | 5/2006 |
| WO | WO 2006/055918 | 5/2006 |
| WO | WO 2006/056427 | 6/2006 |
| WO | WO 2006/060122 | 6/2006 |
| WO | WO 2006/066079 A2 | 6/2006 |
| WO | WO 2006/076681 | 7/2006 |
| WO | WO 2006/079021 | 7/2006 |
| WO | WO 2006/107859 | 10/2006 |
| WO | WO 2006/107860 | 10/2006 |
| WO | WO 2006/116713 | 11/2006 |
| WO | WO 2006/122154 | 11/2006 |
| WO | WO 2006/133147 | 12/2006 |
| WO | WO 2006/138418 | 12/2006 |
| WO | WO 2007/008548 | 1/2007 |
| WO | WO 2007/044796 | 4/2007 |
| WO | WO 2007/048065 | 4/2007 |
| WO | WO 2007/053685 | 5/2007 |
| WO | WO 2007/062167 | 5/2007 |
| WO | WO 2007/064797 | 6/2007 |
| WO | WO 2007/100990 | 9/2007 |
| WO | WO 2007/104034 | 9/2007 |
| WO | WO 2007/107545 | 9/2007 |
| WO | WO 2007/108968 | 9/2007 |
| WO | WO 2007/117482 | 10/2007 |
| WO | WO 2007/117559 | 10/2007 |
| WO | WO 2007/117778 | 10/2007 |
| WO | WO 2007/120842 | 10/2007 |
| WO | WO 2007/127474 | 11/2007 |

OTHER PUBLICATIONS

Anonymous, Verfahren zur Hestellung von 6-Arylyridazinon-3 Verbindungen, (Mar. 1999), Research Disclosure No. 311123, The Industry Standard Disclosure Publication Service, Questel Ireland Ltd., pp. 1-5.
Australian Office Action dated Dec. 15, 2010 in Application No. 2006244072, filed May 9, 2006.
Australian Office Action dated Jan. 10, 2012 in Application No. 2006244072, filed May 9, 2006.
Azuma et al., A placebo control and double blind phase II clinical study of pirfenidone in patients with idiopathic pulmanory fibrosis in Japan, Am J Respir Crit Care Med., (2002) 165: A729.
Badger et al., Pharmacological profile of SB 203580, a selective inhibitor of cytokine suppressive binding protein/p38 kinase, in animal models of arthritis, bone resorption, endotoxin shock and immune function. J Pharmacol Exp Ther., (Dec. 1996) 279(3): 1453-1461.
Boehm et al., New Inhibitors of p38 Kinase. Expert Opin Ther Pat (2000), 10(1): 25-37.
Border et al., Transforming growth factor beta in tissue fibrosis, N Engl J Med., (1994) 331(19): 1286-1292.
Brinkman et al., Engagement of Tumor Necrosis Factor (TNF) Receptor 1 Leads to ATF-2- and p38 Mitogen-activated Protein Kinase-dependent TNF-alpha Gene Expression, J Biol Chem., (Oct. 1999) 274(43): 20882-30886.
Cambpell et al., A Novel Mechanism for TNF-alpha Regulation by p38 MAPK: Involvement of NF-kB with Implications for Therapy in Rheumatoid Arthritis, J Immunol., (2004) 173(11): 6928-6937.
Canadian Office Action dated Jun. 8, 2012 for Application No. 2,608,116, filed May 9, 2006.
Chinese Office Action dated Dec. 9, 2011 for Application No. 200600251605, filed May 9, 2006.
Chinese Office Action dated Mar. 11, 2010 for Application No. 200600251605, filed May 9, 2006.
Columbian Office Action dated Dec. 15, 2011 for Application No. 07117657, filed May 9, 2006.
Columbian Office Action dated May 24, 2011 for Application No. 07117657, filed May. 9, 2006.
Dong et al., MAP kinases in the immune response, Annu Rev Immunol., (2002) 20: 55-72.
Elbashir et al., Duplexes of 21-nucleotide RNAs mediate RNA interference in cultured mammalian Cells, Nature (2001) 411(6836): 494-498.
English et al., Pharmacological inhibitors of MAPK pathways, Trends Pharmacol Sci., (2002) 23(1): 40-45.
Erian et al., Beta-Enaminonitriles in heterocyclic synthesis; Pyridines, pyrimidines and pyrazoles as antibacterial agents, Scientia Pharmaceutica (Dec. 1999) 67(4): 253-261.
European Office Action dated Aug. 17, 2012 in Application No. 06759440.8, filed May 9, 2006.
European Office Action dated Jan. 25, 2012 for Application No. 6759440.8, filed May 9, 2006.
Fitzgerald et al., Structural basis for p38alpha MAP kinase quinazolinone and pyridol-pyrimidine inhibitor specificity, Nat Struct Biol (2003) 10(9): 764-769.
Fuchs et al., Stability of the ATF2 Transcription Factor is Regulated by Phosphorylation and Dephosphorylation, J Biol Chem., (Apr. 2000), 275(17): 12560-12564.
Furukawa et al., p38 MAPK mediates fibrogenic signal through Smad3 phosphorylation in rat myofibroblasts, Hepatology (2003) 38(4): 879-889.
Gahl et al., Effect of pirfenidone on the pulmonary fibrosis of Hermansky-Pudlak syndrome, Mol Genet Metab., (Jul. 2002) 76(3): 234-242.
Greene et al, Protective Groups in Organic Synthesis. John Wiley & Sons, 3rd Edition, 1999, Table of Contents Only.
Griswold et al., Differentiation in vivo of Classical Non-Steroidal Antiinflammatory Drugs from Cytokine Suppressive Antiinflammatory Drugs and other Pharmacological Classes Using Mouse Tumour Necrosis Factor Alpha Production, Drugs Exp Clin Res. (1993) 19(6): 243-248.
Higuchi et al., Pro-drugs as a Novel Drug Delivery System, (1975) vol. 14, A.C.S. Symposium Series, Table of Content Only.
Indonesia Office Action dated Oct. 7, 2012 for Application No. W 00200703614, filed May 9, 2006.
IPRP and WO dated Nov. 13, 2007 for PCT/US2006/017988, filed May 9, 2006.
ISR dated May 29, 2007 for PCT/US2006/017988, filed May 9, 2006.
Israel Office Action dated Dec. 27, 2013 for Application No. 186731, filed May 9, 2006.
Japanese Office Action dated Nov. 24, 2011 for Application No. 2008-511290, filed May 9, 2006.
Jiang et al., Characterization of the Structure and Function of a New Mitogen-activated Protein Kinase (p38-beta). J Biol Chem. (Jul. 1996) 271(30): 17920-17926.
Joe et al., Animal Models of Rheumatoid Arthritis and Related Inflammation, Curr Rheumatol Rep. 1: 139-148.
Kaminska et al., TGF beta signalling and its role in tumour pathogenesis, Acta Biochim Pol., (Jun. 2005) 52(2): 329-337.
Katritzky et al., J Hetero Chem., Synthesis and Some Transformations 4-Benzotriazolyl-3,4-dihydropyrid-2-ones (1996) 33(6): 2031-2036.
Kisteneva, Azomethine Dyes from Oxindole Derivatives. I, The Journal of General Chemistry of the U.S.S.R. (1956) 26(3): 1327-1332.
Kisteneva, Azomethine Dyes from Oxindole Derivatives. II, The Journal of General Chemistry of the U.S.S.R. (1956) 26(7): 2251-2255.
Ko et al., A New and Facile Synthesis of 2-Pyridones, (2001) 22(2): 234-236.
Kumar et al., Novel Homologues of CSBP/P38 MAP Kinase: Activation, Substrate, Specificity and Sensitivity to Inhibition by Pyridinyl Imidazoles, Biochem Biophys Res Comm., (1997) 235: 533-538.

(56) References Cited

OTHER PUBLICATIONS

Lam et al., Copper-catalyzed general C—N and C—O bond cross-coupling with arylboronic acid, Tetrahedron Lett. (2001) 42: 3415-3418.
Lam et al., Copper-promoted C—N bond cross-coupling with phenylstannane, Tetrahedron Lettrs (2002) 43: 3091-3094.
Laufer et al., An in-vitro screening assay for the detection of inhibitors of proinflammatory cytokine synthesis: a useful tool for the development of new antiarthritic and disease modifying drugs, Osteoarth Cartilage (2002) 10: 961-967.
Laufer et al., From Imidazoles to Pyrimidines: New Inhibitors of Cytokine Release, J Med Chem., (2002) 45: 2733-2740.
Laurent, Biochemical pathways leading to collagen deposition in pulmonary fibrosis, Ciba Found Symp. (1985) 114: 222-233.
Lee et al., A protein kinase involved in the regulation of inflammatory cytokine biosynthesis, Nature (Dec. 1994), 372(22): 740-746.
Lee et al., Bicyclic imidazoles as a novel class of cytokine biosynthesis inhibitors, Ann NY Acad Sci., (1993) 696: 149-170.
Lee et al., Inhibition of Monocyte IL-1 Production by the Anti-inflammatory Compound, SK&F 86002, Int J Immunopharmac., (1988) 10(7): 835-843.
Lee et al., Inhibition of p38 MAP Kinase as a Therapeutic Strategy, Immunopharmaco (2000) 47: 1185-201.
Lee et al., MAP Kinase p38 Inhibitors: Clinical Results and an Intimate Look at Their Interactions with p38alpha Protein, Curr Med Chem. (2005) 12: 2979-2994.
Lee et al., p38 Mitogen-activated Protein Kinase Inhibitors—Mechanisms and Therapeutic Potentials, Pharmacol. Ther., (1999) 82(2-3): 389-397.
Lee et al., Pirfenidone: A Novel Pharmacological Agent That Inhibits Leiomyoma Cell Proliferation and Collagen Production, J Clin Endocrinol Metab. (1998) 83(1): 219-223.
Li et al., The Primary Structure of p38gamma: A New Member of p38 Group of MAP Kinases, Biochem Biophys Res Comm., (1996) 228: 334-340.
Liverton et al., Design and Synthesis of Potent, Selective, and Orally Bioavailable Tetrasubstituted Imidazole Inhibitors of p38 Mitogen-Activated Protein Kinase, J Med Chem. (1999) 42(12): 2180-2190.
Lowery et al., Transcreener: screening enzymes involved in covalent regulation, Expert Opin Ther Targets (Feb. 2006) 10(1): 179-190.
Madagascar Office Action dated May 24, 2012 for Madagascar Application No. 2007/070, filed May 2006.
Matsuoka, et al., A p38 MAPK inhibitor, FR-167653, ameliorates murine bleomycin-induced pulmonary fibrosis, Am J Physiol Lung Cell Mol Physiol., (2002) 283: L103-L112.
Mayer et al., p38 MAP kinase inhibitors: A future therapy for inflammatory diseases, Drug Discovery Today: Therapeutic Strategies/Immunological disorders and autoimmunity, (2006) 3(1): 50-54.
McIntyre et al., Pyridazine Based Inhibitors of p38 MAPK, Bioorg Med Chem Lttr., (2002) 12: 689-692.
Mederski et al., N-Aryl Heterocycles via Coupling Reactions with Arylboronic Acids, Tetrahedron (1999) 55(44): 12757-12770.
Muddu et al., Resolving fibrosis in the diseased liver: translating the scientific promise to the clinic, Int J Biochem Cell Biol., (2007) 39(4): 695-714 [Online Oct. 7, 2006].
Nagai et al., Open-label Compassionate Use One Year-treatment with Pirfenidone to Patients with Chronic Pulmonary Fibrosis, Intern Med., (2002) 41(12): 1118-1123.
Newton et al., New aspects of p38 mitogen activated protein kinase (MAPK) biology in lung inflammation, Drug Discovery Today: Disease Mechanisms, (2006) 3: 53-61.
Nicaraguan Examination Report dated Jul. 6, 2012 for Application No. 2007/0289, filed May 9, 2006.
Nicaraguan Office Action dated Jan. 8, 2013 for Application No. 2007/0289, filed May 9, 2006.

Noble et al., Idiopathic pulmonary fibrosis: new insights into pathogenesis, Clin Chest Med. (2004) 25(4): 749-758.
Ono et al., The p38 Signal Transduction Pathway Activation and Function, Cell Signal., (2000) 12: 1-13.
Ozes et al., 697 Preclinical activity of pirfenidone (5-methyl-1phenyl-2(IH)-pyridone) in cell-based models of nonalcoholic steatohepatitis, Hepatology, (2003) 38: 495.
Pargellis et al., Inhibition of p38 MAP kinase by utilizing a novel allosteric binding site, Nat Struct Biol. (2002) 9(4): 268-272.
Philippine Office Action dated Aug. 17, 2012 for Application No. 12007502446, filed May 9, 2006.
Philippine Office Action dated Oct. 14, 2011 for Application No. 1-2007-502446, filed May 11, 2007.
Przheval'skii et al., Mono(m-substituted) Chloroacetyldiarylamines in the Stollé Reaction, Chem Heterocycl Compd. (1982) 18(7): 716-719.
Raghu et al., Treatment of Idiopathic Pulmonary Fibrosis with a New Antifibrotic Agent, Pirenidone—Results of a Prospective, Open-label Phase II Study, Am J Respir Crit Care Med, (1999) 159: 1061-1069.
Raingeaud et al., Pro-inflammatory Cytokines and Environmental Stress Cause p38 Mitogen-activated Protein Kinase Activation by Dual Phosphorylation on Tyrosine and Threonine, J Biol Chem., (1995) 270(13): 7420-7426.
Richards et al., Biochemical and cellular mechanisms of pulmonary fibrosis, Toxicol Pathol. (1991) 119: 526-539.
Roche et al. (Eds.), Bioveversible Carriers in Drug Design, American Pharmaceutical Association and Pergamon Press (1987) Table of Contents Only.
Salituro et al., Inhibitors of p38 MAP Kinase: Therapeutic Intervention in Cytokine-Mediated Diseases, Curr Med Chem., (1999) 6: 807-823.
Sarges et al., A Novel Class of "GABAergic" Agents: 1-Aryl-3-(aminoalkylidene)oxindoles, (1989) 132(2): 437-444.
Shi-Wen et al., Endothelin-1 Induces Expression of Matrix-associated Genes in Lung Fibroblasts through MEK/ERK. J Biol Chem. (Mar. 23, 2004) 279(22): 23098-23103.
Stambe et al., The Role of p38alpha Mitogen-Activated Protein Kinase Activation in Renal Fibrosis, J Am Soc Nephrol., (2004) 15: 370-379.
Stein et al., p38-2, a Novel Mitogen-activated Protein Kinase with Distinct Properties, J Biol Chem., (1997) 272(31): 19509-19517.
Stollé, Über N-substituierte Oxindole and Isatine, Journal für Praktische Chemie, (1930), 128: 1-43.
Sugahara et al., A Facile copper-catalyzed Ullmann condensation: N-arylation of Heterocyclic compounds containing an-NHCO-moiety, Chem Pharm Bull., (1997) 45(4): 719-721.
Ting et al., Substituted 1,3-Dihydro-2H-pyrrolo[2,3-b]pyridin-2-ones as Potential Antiinflammatory Agents, J Med Chem. (1990) 33(10): 2697-2706.
Trifilieff et al., CGH2466, a combined adenosine receptor antagonist, p38 mitogen-activated protein kinase and phosphodiesterase type 4 inhibitor with potent in vitro and in vivo anti-inflammatory activities, Br J Pharmacol., (Jan. 2005) 144: 1002-1010.
Underwood et al., Inhibition of p38 Map Kinase, Prog Respir Res., (2001) 3'1: 342-345.
Underwood et al., SB 239063, A p38 MAPK inhibitor, reduces neutrophilia, inflammatory cytokines, MMP-9, and fibrosis in lung, Am J Physiol Lung Cell Mol Physiol., (2000) 279: L895-L902.
Uzbekistanian Office Action dated May 29, 2012 in Application No. IAP20070502, filed May 9, 2006.
Vippagunta et al., Crystalline solids, Advanced Drug Delivery Reviews (2001) 48: 3-26.
Wang et al., Molecular Cloning and Characterization of a Novel p38 Mitogen-activated Protein I Kinase, J Biol Chem., (1997) 272(38): 23668-23674.
Wang et al., Requirement of Mitogen-activated Protein Kinase Kinase 3 (MKK3) for Activation of p38α p38σ MAPK Isoforms of TGF-β1 in Murine Mesangial Cells (2002) 277: 47257-47262.
Ammar et al., Cyanoacetanilides Intermediates in Heterocyclic Syntheses. Part 1: A Facile Synthesis of Polysubstituted and Condensed Pyridones. J Chinese Chem Society (2004) 51: 975-981.

(56) References Cited

OTHER PUBLICATIONS

Barluenga et al., Easy Preparation of 2-Methyl-1,3-Dimorpholino-1,3-Butadiene and an Overview of Its Synthetic Applications. Tetrahed Lttrs. (1995) 36(36): 6551-6554.
Beccalli et al., Pd-catalyzed intramolecular cyclization of pyrrolo-2carboxamindes: regiodivergent routes to pyrrolo-pyrazines and pyrrolo-pyridines. Tetrahedron (2005) 61: 1077-1082.
Buysens et al., Intramolecular Diels-Alder Reactions of 2(1H)-Pyrazinones: Synthesis of New Furo/Pyrano-pyridinones and -pyridines. Tetrahedron (1995) 51(45): 12463-12478.
CAS Registry No. 586387-14-6, STN Entry Date: Sep. 16, 2003, 1-Benzyl-4-(benzylthio)-5-methylpyridin-2(1H)-one, 1 page.
Chemical Abstracts Services; CAS Registry No. 102718-41-2; 3,4-Pyridinedicarboxylic acid, 1,6-dihydro-1-(2-hydroxyphenyl)-6-oxo-, 3,4-dimethyl ester; Entered: Jun. 14, 1986; 1 page.
Chemical Abstracts Services; CAS Registry No. 115551-60-5; 2(1H)-Pyridinone, 1-(2,3,4,5,6-pentafluorophenyl)-4-(trifluoromethyl); Entered: Jul. 30, 1988; 1 page.
Chemical Abstracts Services; CAS Registry No. 115551-94-5; 2(1H)-Pyridinone, 1-(4-chloro-2-fluoro-5-hydroxyphenyl)-4-(trifluoromethyl); Entered Apr. 27, 2009; 1 page.
Chemical Abstracts Services; CAS Registry No. 130879-34-4; 3,4-Pyridinedicarboxylic acid, 5-chloro-1, 6-dihydro-1-(4-methoxyphenyl)-6-0x0, 3,4-dimethyl ester; Entered: Dec. 7, 1990; 1 page.
Chemical Abstracts Services; CAS Registry No. 13179-26-5; 2(1H)-Pyridinone, 1-(4-chlorophenyl); Entered: Nov. 16, 1984; 1 page.
Chemical Abstracts Services; CAS Registry No. 145705-06-2; 2(1H)-Pyridinone, 1-(2-fluoro-4-hydroxyphenyl)-4-(trifluoromethyl); Entered: Feb. 4, 1993; 1 page.
Chemical Abstracts Services; CAS Registry No. 145705-07-3; 2(1H)-Pyridinone, 1-(2-fluoro-4-hydroxyphenyl)-5-methyl-4-(trifluoromethyl); Entered: Feb. 4, 1993; 1 page.
Chemical Abstracts Services; CAS Registry No. 145705-09-5; 2(1H)-Pyridinone, 5-chloro-1-(2-fluoro-4-hydroxyphenyl)-4-(trifluoromethyl phenyl]; Entered: Feb. 4, 1993; 1 page.
Chemical Abstracts Services; CAS Registry No. 145705-10-8; 2(1H)-Pyridinone, 5-bromo-1-(2-fluoro-4-hydroxyphenyl)-4-(trifluoromethyl); Entered: Feb. 4, 1993; 1 page.
Chemical Abstracts Services; CAS Registry No. 145705-11-9; 2(1H)-Pyridinone, 5-Ethyl-1-(2-fluoro-4hydroxyphenyl)-4-(trifluoromethyl); Entered: Feb. 4, 1993; 1 page.
Chemical Abstracts Services; CAS Registry No. 222978-30-5; 2(1H)-Pyridinone, 1-(2-methoxyphenyl); Entered: May 14, 1999; 1 page.
Chemical Abstracts Services; CAS Registry No. 222978-31-6; 2(1H)-Pyridinone, 1-(2-hydroxyphenyl); Entered: May 14, 1999; 1 page.
Chemical Abstracts Services; CAS Registry No. 3512-19-4; 2(1H)-Pyridinone, 1-(3-chloropheyl); Entered: Nov. 16, 1984; 1 page.
Chemical Abstracts Services; CAS Registry No. 3512-20-7; 2(1H)-Pyridinone, 1-(3-bromophenyl); Entered: Nov. 16, 1984; 1 page.
Chemical Abstracts Services; CAS Registry No. 3534-60-9; 2(1H)-Pyridinone, 1-(3-hydroxyphenyl); Entered: Nov. 16, 1984; 1 page.
Chemical Abstracts Services; CAS Registry No. 53427-77-3; 2(1H)-Pyridinone, 1-(4-methoxyphenyl)-5-methyl; Entered: Nov. 16, 1984; 1 page.
Chemical Abstracts Services; CAS Registry No. 53427-80-8; 2(1H)-Pyridinone, 1-(4-chlorophenyl)-5-methyl; Entered: Nov. 16, 1984; 1 page.
Chemical Abstracts Services; CAS Registry No. 60532-42-5; 2(1H)-Pyridinone, 1-(4-fluoropheyl); Entered: Nov. 16, 1984; 1 page.
Chemical Abstracts Services; CAS Registry Number: 725256-34-8; 2(1H)-Pyridinone, 1-(3-methoxyphenyl); Entered: Aug. 11, 2004; 1 page.
Chemical Abstracts Services; CAS Registry No. 725256-35-9; 2(1H)-Pyridinone, 1-(3-methoxyphenyl)-5-methyl; Entered: Aug. 11, 2004; 1 page.

Chemical Abstracts Services; CAS Registry No. 725256-36-0; 2(1H)-Pyridinone, 5-chloro-1-(4-methoxyphenyl); Entered: Aug. 11, 2004; American Chemical Society; 1 page.
Chemical Abstracts Services; CAS Registry No. 725256-37-1; 3-Pyridinecarboxylic acid, 1,6-dihydro-1-(3-methoxyphenyl)-6-oxo, ethyl ester; Entered: Aug. 11, 2004; 1 page.
Chemical Abstracts Services; CAS Registry No. 725256-38-2; 2(1H)-Pyridinone, 5-chloro-1-(3-methoxyphenyl); Entered Aug. 11 2004; 1 page.
Chemical Abstracts Services; CAS Registry No. 725256-40-6; 2(1H)-Pyridinone, 1-(4-methoxyphenyl); Entered: Aug. 11, 2004; 1 page.
Chemical Abstracts Services; CAS Registry No. 725256-41-7; 2(1H)-Pyridinone, 5-methoxy-1-(4-methoxyphenyl); Entered: Aug. 11, 2004; 1 page.
Chemical Abstracts Services; CAS Registry No. 725256-42-8; 3-Pyridinecarbosylic acid, 1-6-dihydro-1-(4-methoxyphenyl)-64-oxo-, ethyl ester; Entered: Aug. 11, 2004; 1 page.
Chemical Abstracts Services; CAS Registry No. 725256-43-9; 2(1h)-Pyridinone, 5-chloro-1-(4-methoxyphenyl); Entered: Aug. 11, 2004; American Chemical Society; 1 page.
Chemical Abstracts Services; CAS Registry No. 725256-50-8; 2(1H)-Pyridinone, 1-(4-chlorophenyl)-5-methoxy; Entered: Aug. 11, 2004; 1 page.
Chemical Abstracts Services; CAS Registry No. 725256-51-9; 3-Pyridinecarboxylic acid, 1-(4-chlorophenyl)-1,6-dihydro-6-oxo-, ethyl ester; Entered: Aug. 11, 2004; 1 page.
Chemical Abstracts Services; CAS Registry No. 725256-52-0; 2(1H)-Pyridinone, 5-chloro-1-(4-chlorophenyl); Entered: Aug. 11, 2004; 1 page.
Chemical Abstracts Services; CAS Registry No. 766556-75-6; 2(1H)-Pyridinone, 1-(4-iodophenyl); Entered: Oct. 21, 2004; 1 page.
Chemical Abstracts Services; CAS Registry No. 77095-38-6; 3-Pyridinecarboxylic acid, 5-bromo-1-(5-bromophenyl)-1,6-dihydro-4-methyl-6-oxo; Entered: Nov. 16, 1984; 1 page.
Chemical Abstracts Services; CAS Registry No. 848353-85-5; 2(1H)-Pyridinone, 1-(3-fluorophenyl)-5-methyl; Entered: Apr. 12, 2005; 1 page.
Chemical Abstracts Services; CAS Registry No. 851518-71-3; 2(1H)-Pyridinone, 1-(4-hydoxyphenyl)-5-methyl; Entered: Jun. 2, 2005; 1 page.
Chemical Abstracts Services; CAS Registry No. 859538-51-5; 2(1H)-Pyridinone, 1-(4-hydroxyphenyl); Entered Aug. 11, 2005; 1 page.
Chemical Abstracts Services; CAS Registry No. 873969-21-2; 2(1H)-Pyridinone, 1-(2,5-dimethoxyphenyl); Entered: Feb. 10, 2006; 1 page.
Chemical Abstracts Services; CAS Registry No. 873969-22-3; 2(1H)-Pyridinone, 1-(2,3-dimethoxyphenyl); Entered: Feb. 10, 2006; 1 page.
Eiden et al., 6-Styryl-4-methoxy-2-pyridon-Derivate. Archiv der Pharmazie & Berichte der Deutschen Pharmazeutischen Gesellschaft (1971) 304(10): 723-729.
Giri et al., Pharmacokinetics and Metabolism of a Novel Antifibrotic Drug Pirfenidone, in Mice Following Intravenous Administration, Biopharm Drug Disp. (2002) 23: 203-211.
Kane et al., "Reactions of Diazenediyl Compounds with Pyridones: A Novel [4+2] Cycloaddition," J Heter Chem. (1976) 13(3): 673-674.
Kappe et al., Syntheses of Heterocycles, CLXII: The Synthesis of N-Malonylheterocycles., Monatsheft Chemie (1972); 103(2): 586-598.
Ma et al., "Synthesis and biological evaluation of the pirfenidone derivatives as antifibrotic agents", Bioorg Med Chem Lttrs (2013)—Available Online Nov. 25, 2013 at http://dx.doi.org/10.1016/j.bmcl. 2013.11.038; 14 pages.
Patani et al., Bioisosterism: A Rational Approach in Drug Design. Chem. Rev. (1996), 96(8): 3147-3176.
Pednekar et al., Synthesis of Substituted Pyridazinones and Some Novel Fused Heterocycles from Pyran-2-One and Pyridin-2-One Systems, Indian J Heter Chem. (1998) 8(2): 89-94.

(56) References Cited

OTHER PUBLICATIONS

Results from Chemical Abstract Services Search of Sep. 4, 2013 in Registry/CAPLUS 1907—date, CASREACT, 1840—date, and WPINDEX DCR 1999—date. Answers 1-130 are to patent documents and answers 131-214 are to non-patent literature. One exemplary structure was displaced for Answers 1-130; pp. 291.

Results from Chemical Abstract Services Search of Sep. 4, 2013 showing 3161 structures that were registered from other sources such as chemical libraries and do not have any literature associated with them. Each compound is identified by CA Index name, molecular formula, and structure; pp. 1051.

Simonsen et al., Ethyl 6-Methyl-2-pyrone-3, 5-dicarboxylate and its derivatives. J Chem Soc Trans. (1908) 93: 1022-1032.

Wang et al., An improved Ullmann-Ukita-Buchwald-Li conditions for CuI-catalyzed coupling reaction of 2-pyridones with aryl halides, Tetrahedron (2005) 61(11): 2931-2939.

Yan et al., Pirfenidone effect and mechanism in the treatment of fibrotic diseases. West China Medical Journal (2004) 19(1):169-170 [with English machine translation].

Zohdi et al., Heterocyclic Synthesis with Isothiocyanate and sulfur: A novel route for the synthesis of Pyridino[2,3-d]Pyridazine and Thiazolo[4,5-b]Isoquinoline derivatives. Phosphorus, Sulfur, and Silicon (1995) 101(1-4), 179-187.

Australian Examination Report dated Aug. 30, 2013 in Application No. 2012216834, filed Sep. 13, 2012.

Canadian Office Action dated Mar. 15, 2013 for Application No. 2,608,116, filed May 9, 2006.

Canadian Office Action dated Mar. 19, 2014 for Application No. 2,608,116, filed May 9, 2006.

Chinese Office Action dated Apr. 3, 2014 for Patent Application No. 201210529415.9, filed May 9, 2006.

Chinese Office Action dated Jul. 16, 2015 for Patent Application No. 201210529415.9, filed Dec. 10, 2012.

European Search Report dated Mar. 18, 2013 in Application No. 13154719.2, filed Feb. 18, 2013.

European Office Action dated Mar. 25, 2014 for Application No. 13154719.2, filed Feb. 18, 2013.

European Office Action dated Apr. 23, 2015 for Patent Application No. 13154719.2, filed Feb. 8, 2013.

Indian Examination Report dated Mar. 26, 2013 for Application No. 8551/DELNP/2007, filed May 9, 2006.

Israel Office Action dated Mar. 20, 2014 for Application No. 186731, filed May 9, 2006.

Japanese Office Action dated Oct. 4, 2013 for Application No. 2008-511290, filed May 9, 2006.

Japanese Office Action dated Nov. 15, 2013 for Application No. 2012-069834, filed May 9, 2006.

Japanese Office Action dated Aug. 25, 2014 for Application No. 2012-069834, filed May 9, 2006.

Japanese Office Action dated Aug. 25, 2014 for Application No. 2012-069833, filed May 9, 2006.

Korean Office Action dated Mar. 20, 2013 for Application No. 10-2007-7028127, filed May 9, 2006.

Korean Office Action dated May 13, 2014 for Application No. 10-2007-7028127, filed May 9, 2006.

Akiyama et al., Autoantibody against activating transcription factor-2 in patients with systemic sclerosis, *Clin. Exp. Rheumatol.*, 27:751-7 (2009).

Matsuoka et al., A p38 MAPK inhibitor, FR-167653, ameliorates murine bleomycin-induced pulmonary fibrosis, *Am. J. Physiol. Lung Cell Mol. Physiol.*, 283:L103-12 (2002).

METHOD OF MODULATING STRESS-ACTIVATED PROTEIN KINASE SYSTEM

CROSS REFERENCE TO RELATED APPLICATIONS

This is a divisional of U.S. application Ser. No. 14/263,787, filed Apr. 28, 2014; which is a continuation of U.S. application Ser. No. 13/528,624, filed Jun. 20, 2012, now U.S. Pat. No. 8,741,936; which is a continuation of U.S. application Ser. No. 12/790,099, filed May 28, 2010, now abandoned; which is a divisional of U.S. application Ser. No. 11/431,132, filed May 9, 2006, now U.S. Pat. No. 7,728,013; and which claims the benefit of priority to U.S. Provisional Patent Application No. 60/679,471 filed on May 10, 2005, and U.S. Provisional Patent Application No. 60/732,230 filed on Nov. 1, 2005, each of which is hereby expressly incorporated by reference in its entirety.

FIELD OF THE INVENTION

This invention relates to compounds and methods useful in treating various inflammatory conditions and/or fibrotic conditions, including those associated with enhanced activity of kinase p38.

BACKGROUND OF THE INVENTION

A large number of chronic and acute conditions have been recognized to be associated with perturbation of the inflammatory response. A large number of cytokines participate in this response, including IL-1, IL-6, IL-8 and TNFα. It appears that the activity of these cytokines in the regulation of inflammation may be associated with the activation of an enzyme of the cell signaling pathway, a member of the MAP kinase family generally known as p38 and also known as SAPK, CSBP and RK.

Several inhibitors of p38, such as NPC 31169, SB239063, SB203580, FR-167653, and pirfenidone have been tested in vitro and/or in vivo and found to be effective for modulating inflammatory responses.

There continues to be a need for safe and effective drugs to treat various inflammatory conditions and/or fibrotic conditions such as inflammatory pulmonary fibrosis and/or idiopathic pulmonary fibrosis.

SUMMARY OF THE INVENTION

One embodiment of the present invention is a method of modulating a stress activated protein kinase (SAPK) system, including contacting a compound with a p38 mitogen-activated protein kinase (MAPK), wherein the compound exhibits an $EC_{50}$ in the range of about 1 μM to about 1000 μM for inhibition of at least one p38 MAPK; and wherein the contacting is conducted at a SAPK-modulating concentration that is less than an $EC_{30}$ for inhibition of the at least one p38 MAPK by the compound.

Another embodiment of the present invention is a method of treating or preventing a disease state in a subject, including, identifying a subject at risk for or having a condition selected from an inflammatory condition and a fibrotic condition; administering a compound to the subject in an effective amount to treat or prevent the condition; wherein the compound exhibits an $EC_{50}$ in the range of about 1 μM to about 1000 μM for inhibition of at least one p38 MAPK; and wherein the effective amount produces a blood or serum or another bodily fluid concentration that is less than an $EC_{30}$ for inhibition of the at least one p38 MAPK.

Another embodiment of the present invention is a method of identifying a pharmaceutically active compound, including: providing a library of compounds; assaying a plurality of compounds from the library for inhibition of at least one p38 MAPK; and selecting at least one compound from the plurality of compounds, wherein the selected compound exhibits an $EC_{50}$ in the range of about 1 μM to about 1000 μM for inhibition of the at least one p38 MAPK.

Another embodiment of the present invention is a method of identifying a pharmaceutically active compound, including: providing a library of compounds; assaying a plurality of compounds from the library for inhibition of TNFα secretion in a bodily fluid in vivo; and selecting at least one compound from the plurality of compounds, wherein the selected compound exhibits an $EC_{50}$ in the range of about 1 μM to about 1000 μM for inhibition of TNFα secretion in a bodily fluid in vivo.

Another embodiment of the present invention is a method of identifying a pharmaceutically active compound, including: providing a library of compounds; assaying a plurality of compounds from the library for inhibition of TNFα secretion by cultured cells in vitro; and selecting at least one compound from the plurality of compounds, wherein the selected compound exhibits an $EC_{50}$ in the range of about 1 μM to about 1000 μM for inhibition of TNFα secretion by cultured cell in vitro.

Another embodiment of the present invention is a method of identifying a pharmaceutically active compound, including: providing a library of compounds; assaying a plurality of compounds from the library for inhibition of TNFα secretion in a bodily fluid in vivo; and selecting at least one compound from the plurality of compounds, wherein the selected compound exhibits an $EC_{50}$ in the range of about 1 μM to about 1000 μM for inhibition of TNFα secretion by cultured cells in vitro.

Another embodiment of the present invention is a method of identifying a pharmaceutically active compound, including: providing a library of compounds; assaying a plurality of compounds from the library for inhibition of TNFα secretion by cultured cells in vitro; and selecting at least one compound from the plurality of compounds, wherein the selected compound exhibits an $EC_{50}$ in the range of about 1 μM to about 1000 μM for inhibition of TNFα secretion in a bodily fluid in vivo.

Another embodiment of the present invention is a compound having the formula of Subgenus III:

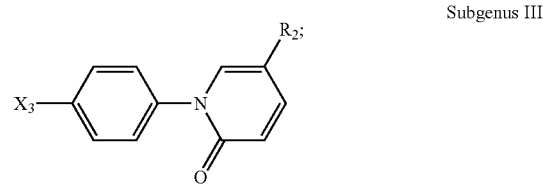

Subgenus III

Wherein $X_3$ is selected from the group consisting of H, F, and OH; and $R_2$ is selected from the group consisting of H and $CF_3$; and wherein the compound exhibits an $EC_{50}$ in the range of about 1 μM to about 1000 μM for inhibition of p38 MAPK; or a pharmaceutically acceptable salt, ester, solvate or prodrug of the compound.

Another embodiment of the present invention is a compound having the formula of Genus VI:

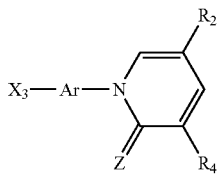

Genus VI

Wherein Ar is pyridinyl or phenyl; Z is O or S; $X_3$ is H, F, Cl, OH, or $OCH_3$; $R_2$ is methyl, C(=O)H, C(=O)$CH_3$, C(=O)O-glucosyl, fluoromethyl, difluoromethyl, trifluoromethyl, methylmethoxyl, methylhydroxyl, or phenyl; and $R_4$ is H or hydroxyl; with the proviso that when $R_2$ is trifluoromethyl, Z is O, $R_4$ is H and Ar is phenyl, the phenyl is not solely substituted at the 4' position by H, F, or OH; wherein the compound exhibits an $EC_{50}$ in the range of about 1 μM to about 1000 μM for inhibition of p38 MAPK; or a pharmaceutically acceptable salt, ester, solvate or prodrug of the compound.

Another embodiment of the present invention is a compound having the formula of Genus VII:

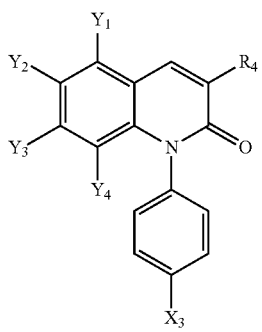

Genus VII

Wherein $X_3$ is H, halogen, $C_1$-$C_{10}$ alkoxy, or OH; $Y_1$, $Y_2$, $Y_3$, and $Y_4$ are independently selected from the group consisting of H, $C_1$-$C_{10}$ alkyl, substituted $C_1$-$C_{10}$ alkyl, $C_1$-$C_{10}$ alkenyl, $C_1$-$C_{10}$ haloalkyl, $C_1$-$C_{10}$ nitroalkyl, $C_1$-$C_{10}$ thioalkyl, $C_1$-$C_{10}$ hydroxyalkyl, $C_1$-$C_{10}$ alkoxy, phenyl, substituted phenyl, halogen, hydroxyl, $C_1$-$C_{10}$ alkoxyalkyl, $C_1$-$C_{10}$ carboxy, $C_1$-$C_{10}$ alkoxycarbonyl; $R_4$ is H, halogen, or OH; and wherein the compound exhibits an $EC_{50}$ in the range of about 1 μM to about 1000 μM for inhibition of p38 MAPK; or a pharmaceutically acceptable salt, ester, solvate or prodrug of the compound.

A further embodiment of the present invention is a pharmaceutical composition containing a compound having a formula as described above and a pharmaceutically acceptable excipient.

These and other embodiments are described in greater detail below.

DETAILED DESCRIPTION OF THE PREFERRED EMBODIMENTS

It has now been discovered that a high therapeutic effect in treating various disorders associated with enhanced activity of kinase p38 may be achieved by using a relatively low-potency p38 kinase inhibitor compound.

Therefore, in one embodiment there is provided a method of modulating a stress-activated kinase (SAPK) system by contacting a compound with a p38 mitogen-activated protein kinase (MAPK). A preferred compound exhibits an $EC_{50}$ in the range of about 1 μM to about 1000 μM, preferably about 50 μM to about 650 μM for the inhibition of at least one p38 MAPK. The concentration at which the compound is contacted with the p38 MAPK is generally less than $EC_{30}$ for inhibition of the p38 by this compound. Preferably, the concentration is less than $EC_{20}$, even more preferably, the concentration is less than $EC_{10}$.

"Mitogen-activated protein kinases (MAPKs)" are evolutionarily conserved serine/threonine kinases involved in the regulation of many cellular events. Several MAPK groups have been identified in mammalian cells, including extracellular signal-regulated kinase (ERK), p38, and SAPK/JNK. It is believed that MAPKs are activated by their specific MAPK kinases (MAPKKs): ERK by MEK1 and MEK2, p38 by MKK3 and MKK6, and SAPK/JNK by SEK1 (also known as MKK4) and MKK7 (SEK2). These MAPKKs may also be activated by various MAPKK kinases (MAPKKKs) such as Raf, MLK, MEKK1, TAK1, and ASK1.

Figure 1:
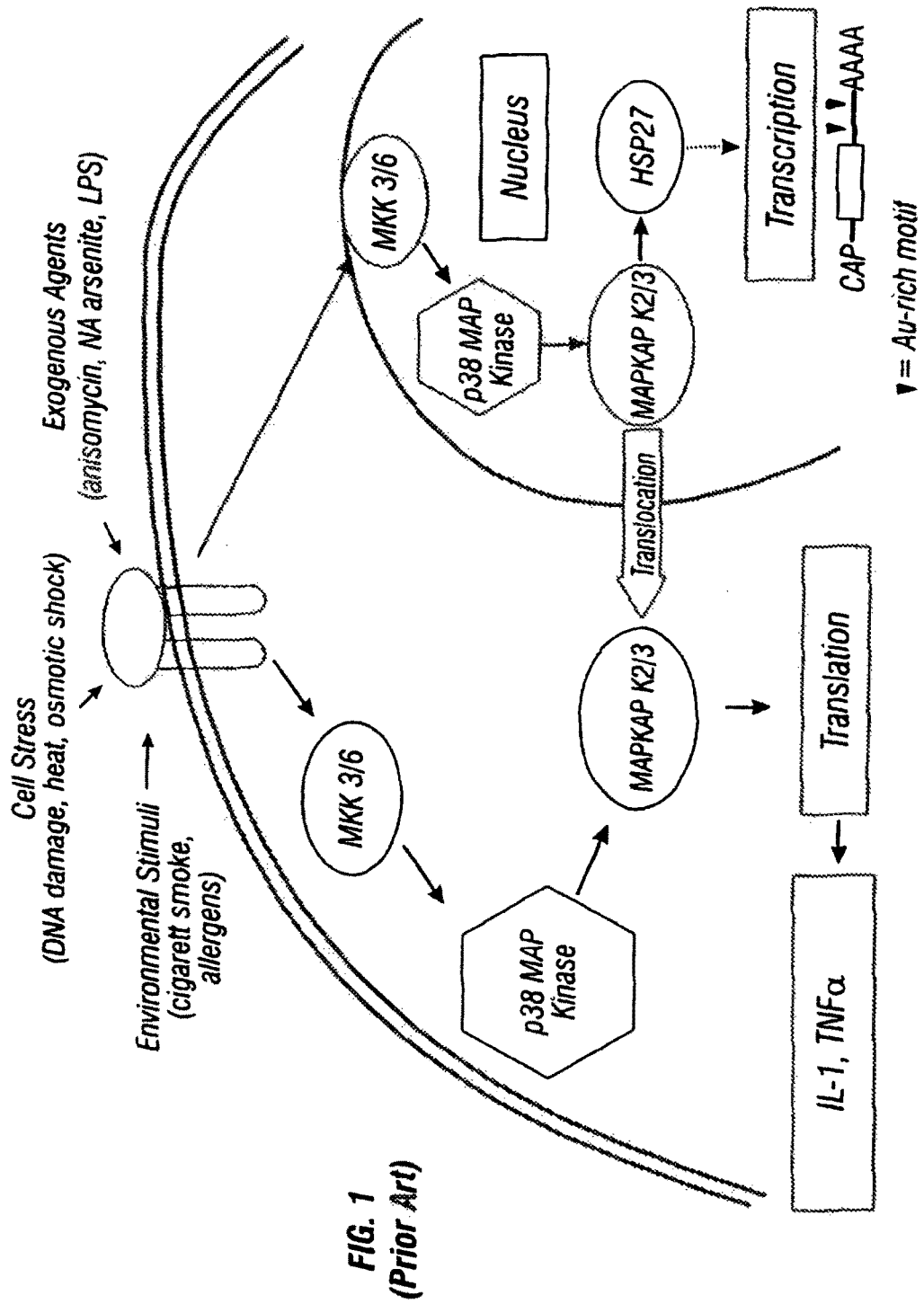
FIG. 1 is a schematic representation of the p38 MAPK signalling cascade (prior art, FIG. 1 from Underwood et al. 2001 Prog Respir Res 31:342-345). This schematic shows activation of the p38 signaling cascade by a variety of stimuli and the downstream effects of p38 activation on an inflammatory response through transcriptional activation and translation/mRNA stabilization.
Figure 2:
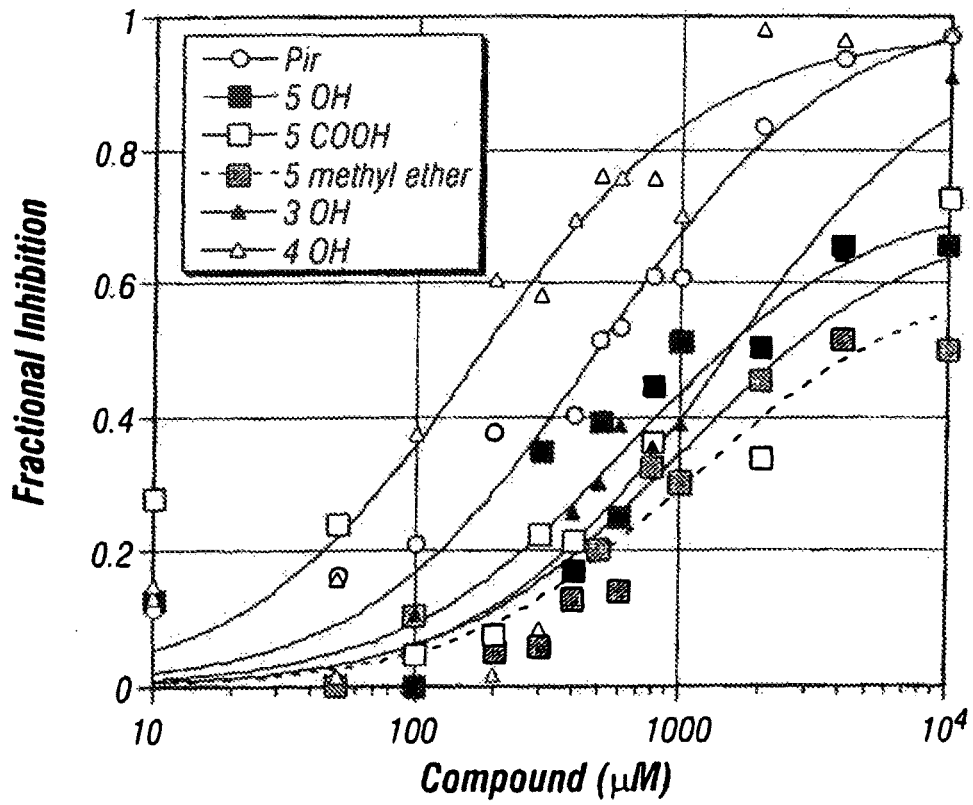
FIG. 2 is a plot showing the fractional inhibition of p38γ by various pirfenidone metabolites and analogs as a function of the concentration of the compounds. The EC50 concentrations of these compounds are shown to the right of the plot. A detailed description of the assay can be found in Example 5.
Figure 3:
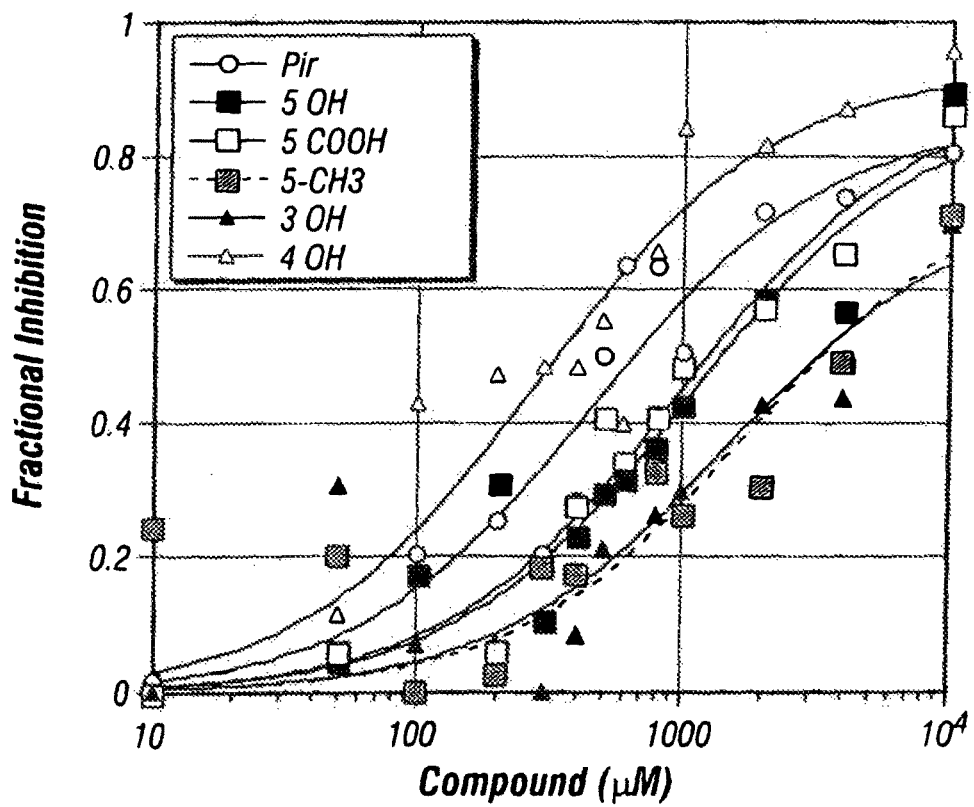
FIG. 3 is a plot showing the fractional inhibition of p38α by various pirfenidone metabolites and analogs as a function of the concentration of the compounds. The $EC_{50}$ concentrations of these compounds are shown to the right of the plot. A detailed description of the assay can be found in Example 5.
Figure 4:
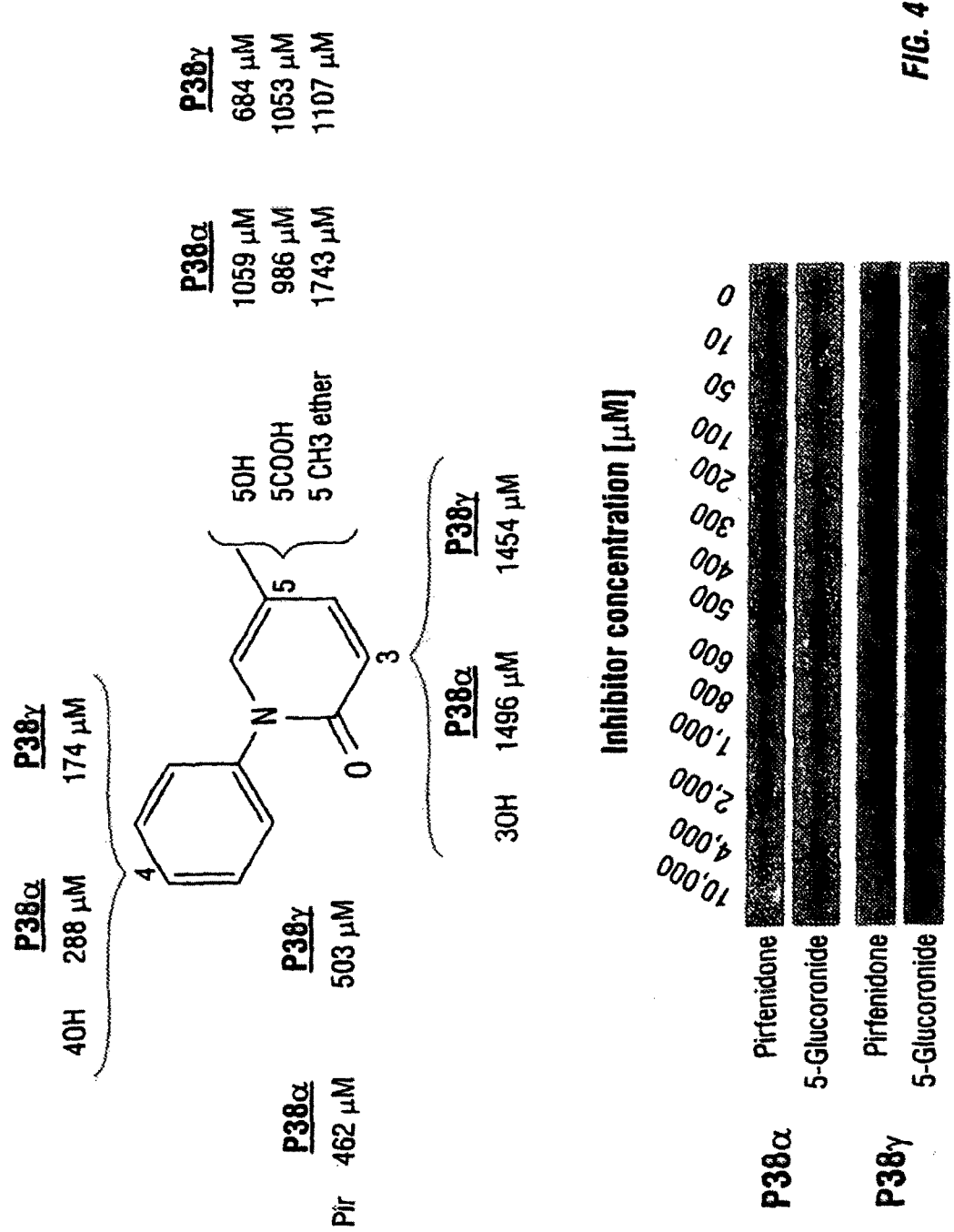
FIG. 4 is a summary of the biochemical data for various pirfenidone metabolites and analogs. The pirfenidone metabolites and analogs referred to in FIGS. 2, 3, 5, and 6 are described by the substitution pattern shown in FIG. 4. The summary shows the effect of substitutions at three positions on the EC50 concentrations for inhibition of p38α and p38γ.
Figure 5:
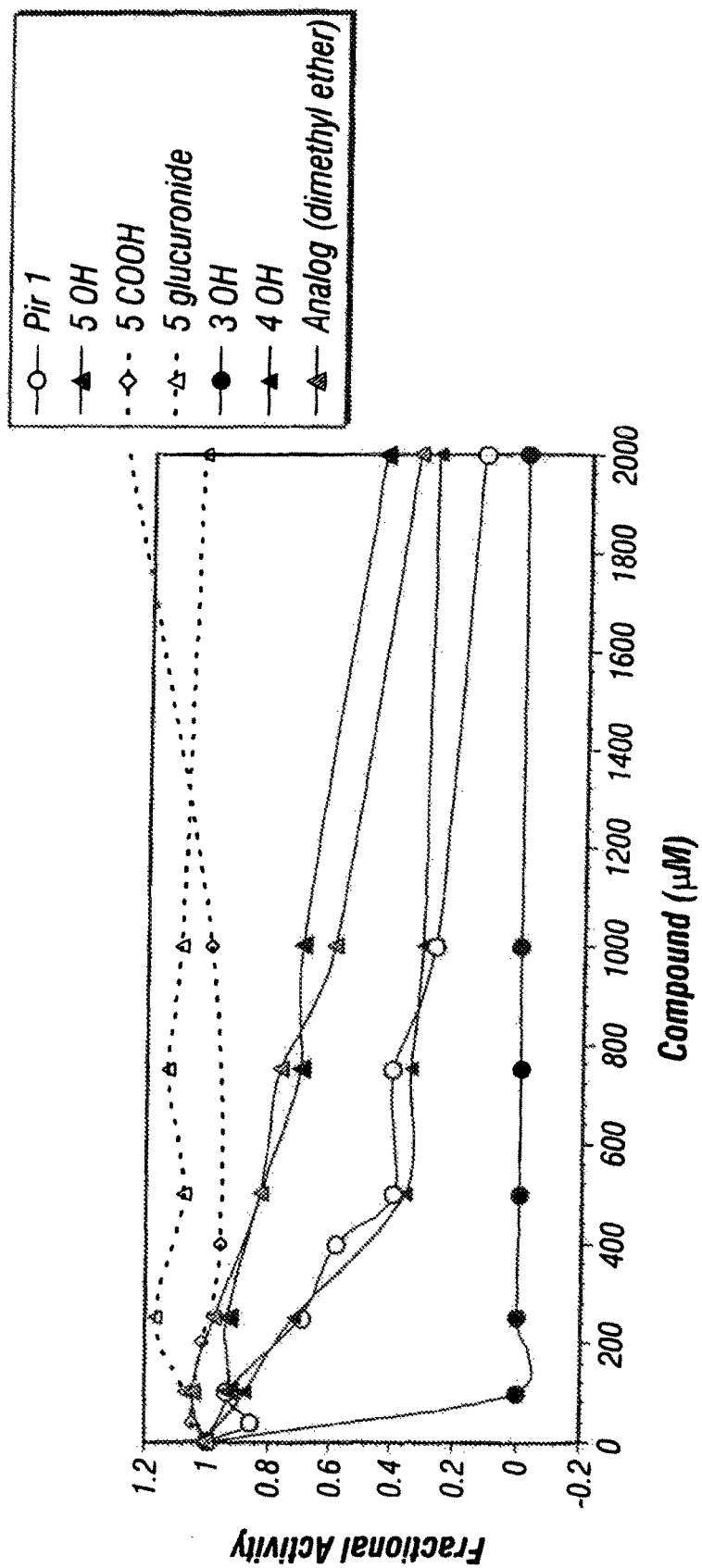
FIG. 5 is a plot showing the fractional activity (TNFα release from macrophage in response to LPS) of various pirfenidone metabolites and analogs as a function of the concentration of each compound. A detailed description of the assay can be found in Example 5.
Figure 6:
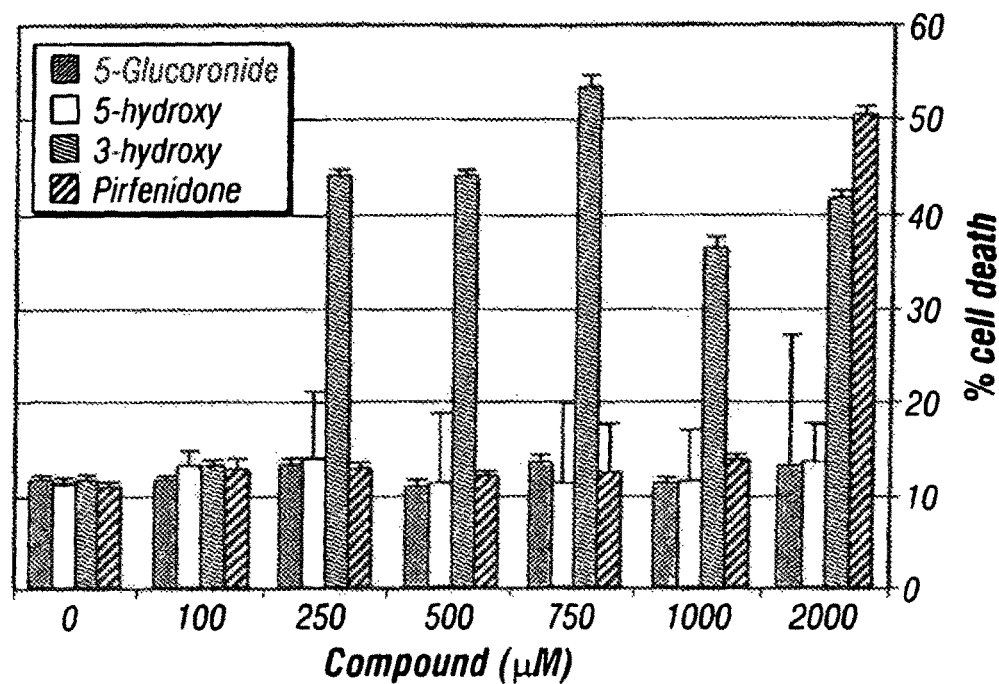
FIG. 6 is a series of bar charts showing the cytotoxicity of various pirfenidone metabolites and analogs at various concentrations of the compounds. Cytotoxicity was determined by measuring LDH release following incubation of cells in the presence of the compound. The amount of LDH released is normalized to that released upon treatment with Triton-X-100 and plotted versus compound concentration.
Figure 6:
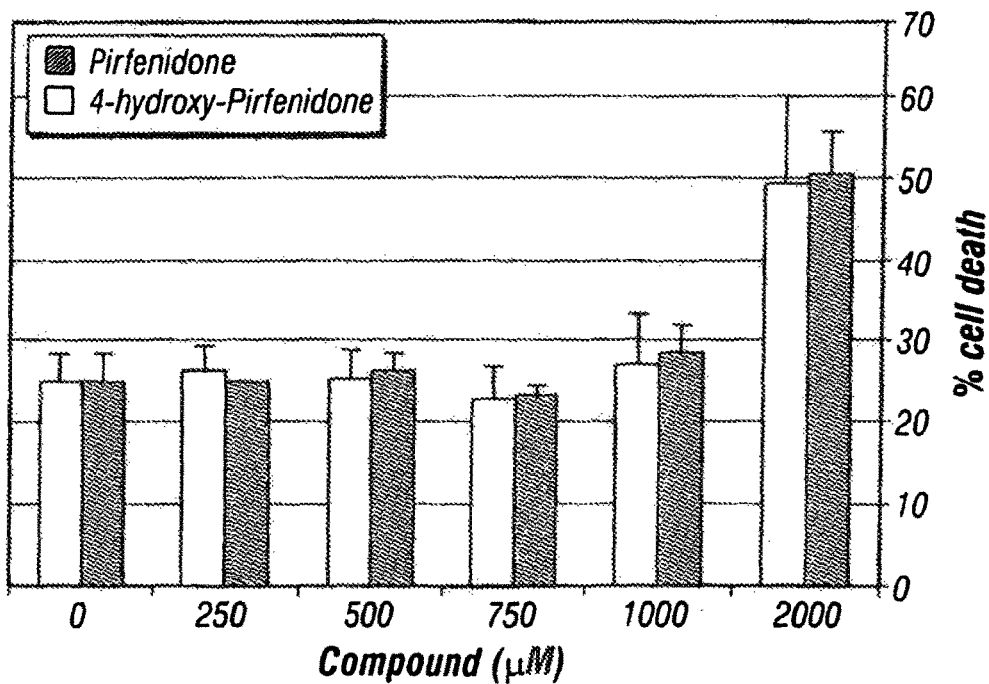
Figure 6:
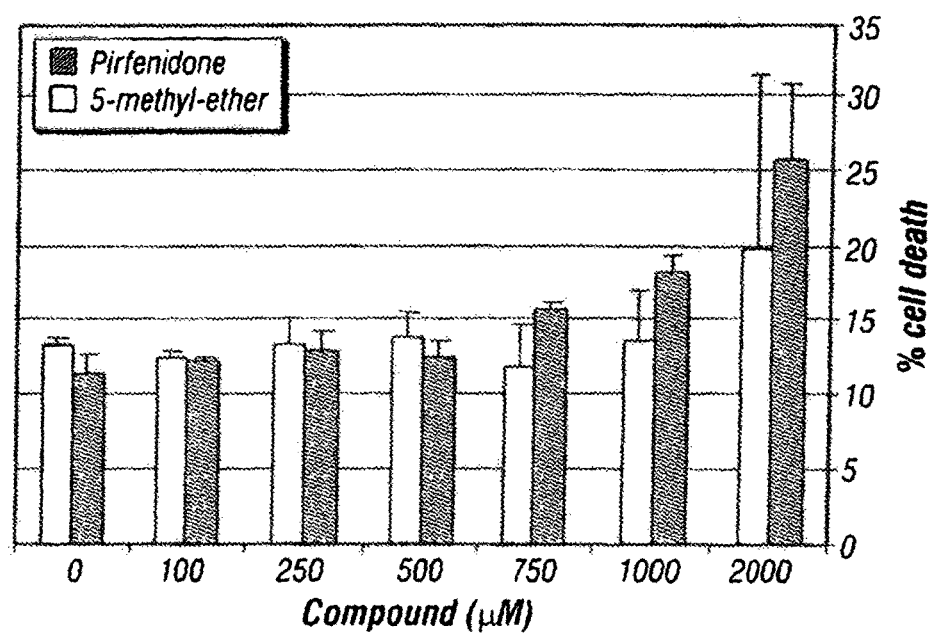

It is believed that the MAPK network involves at least twelve cloned highly conserved, proline-directed serine-threonine kinases which, when activated by cell stresses (oxidative stress, DNA damage, heat or osmotic shock, ultraviolet irradiation, ischemia-reperfusion), exogenous agents (anisomycin, Na arsenite, lipopolysaccharide, LPS) or pro-inflammatory cytokines, TNF-α and IL-1β, can phosphorylate and activate other kinases or nuclear proteins such as transcription factors in either the cytoplasm or the nucleus (FIG. 1).

p38 MAPK

As used herein, "p38 MAPK" is a member of the stress-activated protein kinase family, which includes at least 4 isoforms (α, β, γ, δ), several of which are considered important in processes critical to the inflammatory response and tissue remodeling (Lee et al. 2000 *Immunopharmacol.* 47:185-201). The predominant kinases in monocytes and macrophages, p38α and p38β, appear more widely expressed compared to p38γ (skeletal muscle) or p38δ (testes, pancreas, prostate, small intestine, and in salivary, pituitary and adrenal glands). The p38γ isoform is expressed in myofibroblasts, which have some phenotypic similarities to muscle cells including expression of alpha-smooth muscle actin. A number of substrates of p38 MAP kinase have been identified including other kinases (MAPKAP K2/3, PRAK, MNK 1/2, MSK1/RLPK, RSK-B), transcription factors (ATF2/6, myocyte enhancer factor 2, nuclear transcription factor-β, CHOP/GADD153, Elk1 and SAP-1A1) and cytosolic proteins (stathmin), many of which are important physiologically.

Jiang, Y. et al. 1996 *J Biol Chem* 271:17920-17926 reported characterization of p38β as a 372-amino acid protein closely related to p38-α. Both p38α and p38β are activated by proinflammatory cytokines and environmental stress, p38β is preferentially activated by MAP kinase kinase-6 (MKK6) and preferentially phosphorylate activated transcription factor 2 (ATF2). Kumar, S. et al. 1997 *Biochem Biophys Res Comm* 235:533-538 and Stein, B. et al. 1997 *J Biol Chem* 272:19509-19517 reported a second isoform of p38β, p-38β2, containing 364 amino acids with 73% identity to p38α. It is believed that p38β is activated by proinflammatory cytokines and environmental stress, although the second reported p38β isoform, p38β2, appears to be preferentially expressed in the central nervous system (CNS), heart and skeletal muscle, compared to the more ubiquitous tissue expression of p38α. Furthermore, it is believed that activated transcription factor-2 (ATF-2) is a better substrate for p38β2 than for p38α.

The identification of p38γ was reported by Li, Z. et al. 1996 *Biochem Biophys Res Comm* 228:334-340 and of p38δ by Wang, X. et al. 1997 *J Biol Chem* 272:23668-23674 and by Kumar, S. et al. 1997 *Biochem Biophys Res Comm* 235:533-538. These two p38 isoforms (γ and δ) represent a unique subset of the MAPK family based on their tissue expression patterns, substrate utilization, response to direct and indirect stimuli, and susceptibility to kinase inhibitors. Based upon primary sequence conservation, p38α and β are closely related, but diverge from γ and δ, which are more closely related to each other.

Typically the p38 MAP kinase pathway is directly or indirectly activated by cell surface receptors, such as receptor tyrosine kinases, chemokine or G protein-coupled receptors, which have been activated by a specific ligand, e.g., cytokines, chemokines or lipopolysaccharide (LPS) binding to a cognate receptor. Subsequently, a p38 MAP kinase is activated by phosphorylation on specific threonine and tyrosine residues. After activation, p38 MAP kinase can phosphorylate other intracellular proteins, including protein kinases, and can be translocated to the cell nucleus, where it phosphorylates and activates transcription factors leading to the expression of pro-inflammatory cytokines and other proteins that contribute to the inflammatory response, cell adhesion, and proteolytic degradation. For example, in cells of myeloid lineage, such as macrophages and monocytes, both IL-1β and TNFα are transcribed in response to p38 activation. Subsequent translation and secretion of these and other cytokines initiates a local or systemic inflammatory response in adjacent tissue and through infiltration of leukocytes. While this response is a normal part of physiological responses to cellular stress, acute or chronic cellular stress leads to the excess, unregulated, or excess and unregulated expression of pro-inflammatory cytokines. This, in turn, leads to tissue damage, often resulting in pain and debilitation.

In alveolar macrophages, inhibition of p38 kinases with p38 inhibitor, SB203580, reduces cytokine gene products. It is believed that inflammatory cytokines (TNF-α, IFN-β, IL-4, IL-5) and chemokines (IL-8, RANTES, eotaxin) are capable of regulating or supporting chronic airway inflammation. The production and action of many of the potential mediators of airway inflammation appear to be dependent upon the stress-activated MAP kinase system (SAPK) or p38 kinase cascade (Underwood et al. 2001 *Prog Respir Res* 31:342-345). Activation of the p38 kinase pathway by numerous environmental stimuli results in the elaboration of recognized inflammatory mediators whose production is considered to be translationally regulated. In addition, a variety of inflammatory mediators activate p38 MAPK which may then activate downstream targets of the MAPK system including other kinases or transcription factors, thus creating the potential for an amplified inflammatory process in the lung.

Downstream Substrates of p38 Group of MAP Kinases

Protein kinase substrates of p38α or p38β: MAP kinase-activated protein kinase 2 (MAPKAPK2 or M2), MAP kinase interaction protein kinase (MNK1), p38 regulated/activated kinase (PRAK), mitogen- and stress-activated kinase (MSK: RSK-B or RLPK).

Transcription factors activated by p38: activating transcription factor (ATF)-1, 2 and 6, SRF accessory protein 1 (Sap 1), CHOP (growth arrest and DNA damage inducible gene 153, or GADD153), p53, C/EBPβ, myocyte enhance factor 2C (MEF2C), MEF2A, MITF1, DDIT3, ELK1, NFAT, and high mobility group-box protein (HBP1).

Other types of substrates for p38: cPLA2, $Na^+/H^+$ exchanger isoform-1, tau, keratin 8, and stathmin.

Genes regulated by the p38 pathway: c-jun, c-fos, junB, IL-1, TNF, IL-6, IL-8, MCP-1, VCAM-1, iNOS, PPARγ, cyclooxygenase (COX)-2, collagenase-1 (MMP-1), Collagenase-3 (MMP-13), HIV-LTR, Fgl-2, brain natriuretic peptide (BNP), CD23, CCK, phosphoenolpyruvate carboxykinase-cytosolic, cyclin D1, LDL receptor (Ono et al. 2000 *Cellular Signalling* 12:1-13).

Biological Consequences of p38 Activation p38 and Inflammation

Acute and chronic inflammation are believed to be central to the pathogenesis of many diseases such as rheumatoid arthritis, asthma, chronic obstructive pulmonary disease (COPD) and acute respiratory distress syndrome (ARDS). The activation of the p38 pathway may play an central role in: (1) production of proinflammatory cytokines such as IL-1β, TNF-α and IL-6; (2) induction of enzymes such as COX-2, which controls connective tissue remodeling in pathological condition; (3) expression of an intracellular enzyme such as iNOS, which regulates oxidation; (4) induction of adherent proteins such as VCAM-1 and many other inflammatory related molecules. In addition to these, the p38 pathway may play a regulatory role in the proliferation and differentiation of cells of the immune system. p38 may participate in GM-CSF, CSF, EPO, and CD40-induced cell proliferation and/or differentiation.

The role of the p38 pathway in inflammatory-related diseases was studied in several animal models. Inhibition of p38 by SB203580 reduced mortality in a murine model of endotoxin-induced shock and inhibited the development of mouse collagen-induced arthritis and rat adjuvant arthritis. A recent study showed that SB220025, which is a more potent p38 inhibitor, caused a significant dose-dependent decrease in vascular density of the granuloma. These results indicate that p38 or the components of the p38 pathway can be a therapeutic target for inflammatory disease.

p38 and Apoptosis

It appears that concomitant activation of p38 and apoptosis is induced by a variety of agents such as NGF withdrawal and Fas ligation. Cysteine proteases (caspases) are central to the apoptotic pathway and are expressed as inactive zymogens. Caspase inhibitors may then block p38 activation through Fas cross-linking. However, overexpression of dominant active MKK6b can also induce caspase activity and cell death. The role of p38 in apoptosis is cell type- and stimulus-dependent. While p38 signaling has been shown to promote cell death in some cell lines, in different cell lines p38 has been shown to enhance survival, cell growth, and differentiation.

p38 in the Cell Cycle

Overexpression of p38α in yeast leads to significant slowing of proliferation, indicating involvement of p38α in cell growth. A slower proliferation of cultured mammalian cells was observed when the cells were treated with p38α/β inhibitor, SB203580.

p38 and Cardiomyocyte Hypertrophy

Activation and function of p38 in cardiomyocyte hypertrophy has been studied. During progression of hypertrophy, both p38α and p38β levels were increased and constitutively active MKK3 and MKK6-elicited hypertrophic responses enhanced by sarcomeric organization and elevated atrial natriuretic factor expression. Also, reduced signaling of p38 in the heart promotes myocyte differentiation via a mechanism involving calcineurin-NFAT signaling.

p38 and Development

Despite the non-viability of p38 knockout mice, evidence exists regarding the differential role of p38 in development. p38 has been linked to placental angiogenesis but not cardiovascular development in several studies. Furthermore, p38 has also been linked to erythropoietin expression suggesting a role in erythropoiesis. PRAK has recently been implicated in cell development in murine implantation. PRAK mRNA, as well as p38 isoforms, were found to be expressed throughout blastocyst development p38 and Cell Differentiation p38α and/or p38β were found to play an important role in cell differentiation for several different cell types. The differentiation of 3T3-L1 cells into adipocytes and the differentiation of PC12 cells into neurons both require p38α and/or β. The p38 pathway was found to be necessary and sufficient for SKT6 differentiation into hemoglobinized cells as well as C2C112 differentiation in myotubules.

p38 in Senescence and Tumor Suppression p38 has a role in tumorigenesis and senescence. There have been reports that activation of MKK6 and MKK3 led to a senescent phenotype dependent upon p38 MAPK activity. Also, p38 MAPK activity was shown responsible for senescence in response to telomere shortening, $H_2O_2$ exposure, and chronic RAS oncogene signaling. A common feature of tumor cells is a loss of senescence and p38 is linked to tumorigenesis in certain cells. It has been reported that p38 activation is reduced in tumors and that loss of components of the p38 pathway such as MKK3 and MKK6 resulted in increased proliferation and likelihood of tumorigenic conversion regardless of the cell line or the tumor induction agent used in these studies.

p38 MAP Kinase Inhibitors

A "p38 MAPK inhibitor" is a compound that inhibits the activity of p38. The inhibitory effects of a compound on the activity of p38 may be measured by various methods well-known to a skilled artisan. For example, the inhibitory effects may be measured by measuring the level of inhibition of lipopolysaccharide (LPS)-stimulated cytokine production (Lee et al. 1988 *Int J Immunopharmacol* 10:835-843; Lee et al. 1993 *Ann NY Acad Sci* 696:149-170; Lee et al. 1994 *Nature* 372:739-746; Lee et al. 1999 *Pharmacol Ther* 82:389-397).

Efforts to develop p38 MAPK inhibitors have focused on increasing potency. SB203580 and other 2,4,5-triaryl imidazoles were found to be potent p38 kinase inhibitors with $EC_{50}$ values in nanomolar range. For example, for SB203580 the $EC_{50}$ was found to be 48 nM. The pyridinylimidazoles SKF 86002 (P1) and SB203582 (P2) shown below have been used as the template for the majority of p38 inhibitors. Recent publications (Lee et al. 2000 *Immunopharmacology* 47:185-201) have disclosed the p38 inhibitors (P3-P6) shown below. Notable among these inhibitors is the relatively high potency and selectivity described for compound P4 (p38 $EC_{50}$=0.19 nM) and the inhibition of inflammation driven angiogenesis by SB 220025 (P6).

Two p38 inhibitors reported to be in clinical development are HEP689 (P7) and VX-745 (P8). VX-745 is reportedly in Phase II trials for rheumatoid arthritis. Potent topical anti-inflammatory activity has been disclosed for HRP689, which has reportedly entered clinical development to explore its potential as a topical agent for the treatment of psoriasis and other skin disorders.

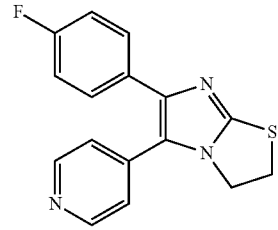

SK&F 86002

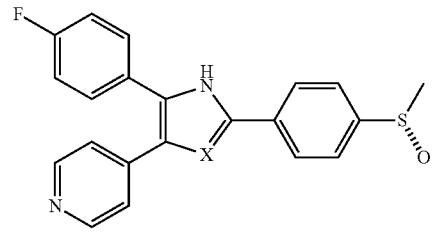

P2 X = N; SB 203580
P3 X = CH; L-167307

-continued

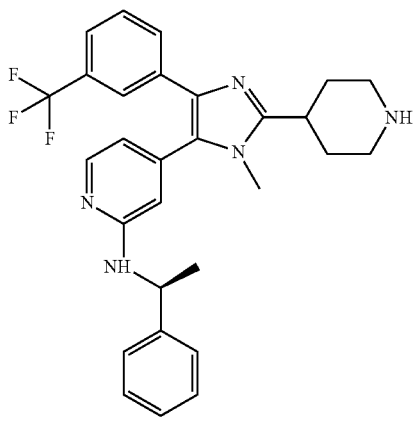
RWJ 68354

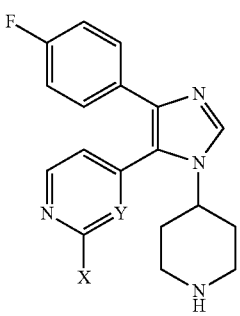
P6 X = H, Y = CH; HEP 689 (SB 235699)
P7 X = HN$_2$, Y = N; SB 220025

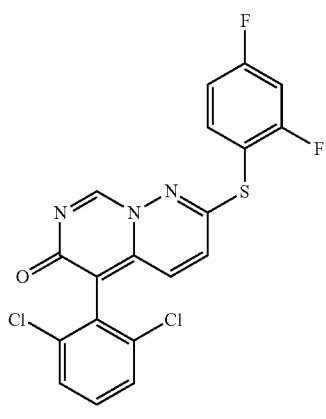
VX-745

Further discussion of various p38 inhibitors can be found in Boehm et al. 2000 *Exp Opin Ther Pat* 10:25-37; and Salituro et al. 1999 *Curr Med Chem* 6:807-823.

Preferred p38 inhibitors described herein are pirfenidone derivatives and analogs that exhibit relatively low potency of p38 inhibition while, surprisingly, still having a relatively high therapeutic effect (e.g., for modulating an SAPK system) as a result of such inhibition. Preferably, the p38 inhibitors of the embodiments exhibit EC$_{50}$ in the range of about 1 μM and about 1000 μM, preferably about 50 μM to about 650 μM for the inhibition of the p38 MAPK.

Pirfenidone Derivatives and Analogs

Pirfenidone (5-methyl-1-phenyl-2-(1H)-pyridone) itself is a known compound and its pharmacological effects are disclosed, for example, in Japanese Patent Application KOKAI (Laid-Open) Nos. 87677/1974 and 1284338/1976. U.S. Pat. No. 3,839,346, issued Oct. 1, 1974; U.S. Pat. No. 3,974,281, issued Aug. 10, 1976; U.S. Pat. No. 4,042,699, issued Aug. 16, 1977; and U.S. Pat. No. 4,052,509, issued Oct. 4, 1977, all of which are hereby incorporated by reference in their entireties, describe methods of manufacture of 5-methyl-1-phenyl-2-(1H)-pyridone and its use as an anti-inflammatory agent.

Pirfenidone and derivatives thereof are useful compounds for modulating a stress activated protein kinase (SAPK) system.

The term "alkyl" used herein refers to a monovalent straight or branched chain radical of from one to ten carbon atoms, including, but not limited to, methyl, ethyl, n-propyl, isopropyl, n-butyl, isobutyl, tert-butyl, n-hexyl, and the like.

The term "alkenyl" used herein refers to a monovalent straight or branched chain radical of from two to ten carbon atoms containing a carbon double bond including, but not limited to, 1-propenyl, 2-propenyl, 2-methyl-1-propenyl, 1-butenyl, 2-butenyl, and the like.

The term "halogen" used herein refers to fluorine, chlorine, bromine, or iodine.

The term "haloalkyl" used herein refers to one or more halogen groups appended to an alkyl radical.

The term "nitroalkyl" used herein refers to one or more nitro groups appended to an alkyl radical.

The term "thioalkyl" used herein refers to one or more thio groups appended to an alkyl radical.

The term "hydroxyalkyl" used herein refers to one or more hydroxy groups appended to an alkyl radical.

The term "alkoxy" used herein refers to straight or branched chain alkyl radical covalently bonded to the parent molecule through an —O— linkage. Examples of alkoxy groups include, but are limited to, methoxy, ethoxy, propoxy, isopropoxy, butoxy, n-butoxy, sec-butoxy, t-butoxy and the like.

The term "alkoxyalkyl" used herein refers to one or more alkoxy groups appended to an alkyl radical.

The term "carboxy" used herein refers to —COOH optionally appended to an alkyl group. Examples of carboxy groups include, but are not limited to, —COOH, —CH$_2$COOH, —CH$_2$CH$_2$COOH, —CH(COOH)(CH$_3$), and the like.

The term "alkoxycarbonyl" refers to —(CO)—O-alkyl. Examples of alkoxycarbonyl groups include, but are limited to, methoxycarbonyl group, ethoxycarbonyl group, propoxycarbonyl group, and the like.

Carbohydrates are polyhydroxy aldehydes or ketones, or substances that yield such compounds upon hydrolysis. Carbohydrates comprise the elements carbon (C), hydrogen (H) and oxygen (O) with a ratio of hydrogen twice that of carbon and oxygen.

In their basic form, carbohydrates are simple sugars or monosaccharides. These simple sugars can combine with each other to form more complex carbohydrates. The combination of two simple sugars is a disaccharide. Carbohydrates consisting of two to ten simple sugars are called oligosaccharides, and those with a larger number are called polysaccharides.

The term "uronide" refers to a monosaccharide having a carboxyl group (—COOH) on the carbon that is not part of the ring. The uronide name retains the root of the monosaccharide, but the -ose sugar suffix is changed to -uronide. For example, the structure of glucuronide corresponds to glucose.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group. When substituted, the substituent group(s) is (are) one or more group(s) individually and independently selected from $C_1$-$C_{10}$ alkyl, $C_1$-$C_{10}$ cycloalkyl, aryl, fused aryl, heterocyclyl, heteroaryl, hydroxy, $C_1$-$C_{10}$ alkoxy, aryloxy, mercapto, $C_1$-$C_{10}$ alkylthio, arylthio, cyano, halogen, carbonyl, thiocarbonyl, $C_1$-$C_{10}$ alkoxycarbonyl, nitro, silyl, trihalomethanesulfonyl, trifluoromethyl, and amino, including mono- and di-substituted amino groups, and the protected derivatives thereof. The protecting groups that can form the protective derivatives of the above substituents are known to those of skill in the art and can be found in references such as Greene and Wuts *Protective Groups in Organic Synthesis*; John Wiley and Sons: New York, 1999. Wherever a substituent is described as "optionally substituted" that substituent can be substituted with the above substituents.

The term "purified" refers to a compound which has been separated from other compounds such that it comprises at least 95% of the measured substance when assayed.

Asymmetric carbon atoms may be present in the compounds described herein. All such isomers, including diastereomers and enantiomers, as well as the mixtures thereof are intended to be included in the scope of the recited compound. In certain cases, compounds can exist in tautomeric forms. All tautomeric forms are intended to be included in the scope of the recited compound. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

Various forms are included in the embodiments, including polymorphs, solvates, hydrates, conformers, salts, and prodrug derivatives. A polymorph is a composition having the same chemical formula, but a different structure. A solvate is a composition formed by solvation (the combination of solvent molecules with molecules or ions of the solute). A hydrate is a compound formed by an incorporation of water. A conformer is a structure that is a conformational isomer. Conformational isomerism is the phenomenon of molecules with the same structural formula but different conformations (conformers) of atoms about a rotating bond. Salts of compounds can be prepared by methods known to those skilled in the art. For example, salts of compounds can be prepared by reacting the appropriate base or acid with a stoichiometric equivalent of the compound. A prodrug is a compound that undergoes biotransformation (chemical conversion) before exhibiting its pharmacological effects. For example, a prodrug can thus be viewed as a drug containing specialized protective groups used in a transient manner to alter or to eliminate undesirable properties in the parent molecule. Thus, reference herein to a compound includes all of the aforementioned forms unless the context clearly dictates otherwise.

The compounds described below are useful in the methods described herein. In an embodiment, a compound as described below exhibits an $EC_{50}$ in the range of about 1 μM to about 1000 μM for inhibition of p38 MAPK.

An embodiment provides a family of compounds represented by the following genus (Genus Ia):

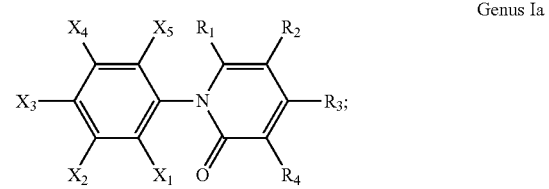

Genus Ia wherein $R_1$, $R_2$, $R_3$, and $R_4$ are independently selected from the group consisting of H, $C_1$-$C_{10}$ alkyl, substituted $C_1$-$C_{10}$ alkyl, $C_1$-$C_{10}$ alkenyl, $C_1$-$C_{10}$ haloalkyl, $C_1$-$C_{10}$ nitroalkyl, $C_1$-$C_{10}$ thioalkyl, $C_1$-$C_{10}$ hydroxyalkyl, $C_1$-$C_{10}$ alkoxy, phenyl, substituted phenyl, halogen, hydroxyl, $C_1$-$C_{10}$ alkoxyalkyl, carboxy, $C_1$-$C_{10}$ alkoxycarbonyl, CO-uronide, CO-monosaccharide, CO-oligosaccharide, and CO-polysaccharide; and $X_1$, $X_2$, $X_3$, $X_4$, and $X_5$ are independently selected from the group consisting of H, halogen, alkoxy, and hydroxy.

Another embodiment provides a family of compounds represented by the following genus (Genus Ib):

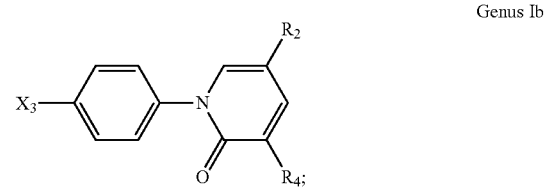

Genus Ib wherein $X_3$ is selected from the group consisting of H, halogen, $C_1$-$C_{10}$ alkoxy, and OH;

$R_2$ is selected from the group consisting of H, halogen, $C_1$-$C_{10}$ alkyl, substituted $C_1$-$C_{10}$ alkyl, $C_1$-$C_{10}$ hydroxyalkyl, $C_1$-$C_{10}$ alkoxyalkyl, $C_1$-$C_{10}$ carboxy, $C_1$-$C_{10}$ alkoxycarbonyl, CO-uronide, CO-monosaccharide, CO-oligosaccharide, and CO-polysaccharide; and $R_4$ is selected from the group consisting of H, halogen, and OH.

Another embodiment provides a family of compounds represented by the following genus (Genus Ic):

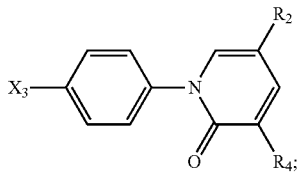

Genus Ic wherein $X_3$ is selected from the group consisting of H, F, OH, and $OCH_3$;

$R_2$ is selected from the group consisting of H, $CF_3$, $CHF_2$, $CH_2F$, $CH_2OH$, COOH, CO-Glucoronide, Br, $CH_3$, and $CH_2OCH_3$; and $R_4$ is selected from the group consisting of H and OH;

with the proviso that when $R_4$ and $X_3$ are H, $R_2$ is not $CH_3$.

Another embodiment provides a family of compounds represented by the following subgenus (Subgenus II):

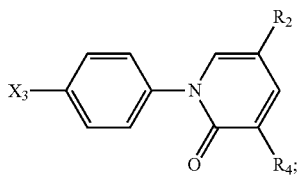

Subgenus II wherein $X_3$ is selected from the group consisting of H, OH, and $OCH_3$;

$R_2$ is selected from the group consisting of H, $CH_2OH$, COOH, CO-Glucoronide, Br, $CH_3$, and $CH_2OCH_3$; and $R_4$ is selected from the group consisting of H and OH, with the proviso that when $X_3$ is OH then $R_2$ is not $CH_3$.

Another embodiment provides a family of compounds represented by the following subgenus (Subgenus III):

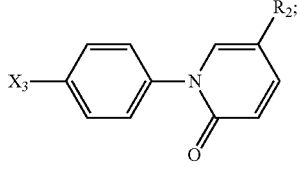

Subgenus III wherein $X_3$ is selected from the group consisting of H, F, and OH; and $R_2$ is selected from the group consisting of H, Br, $CH_2F$, $CHF_2$, and $CF_3$.

Another embodiment provides a family of compounds represented by the following subgenus (Subgenus IV):

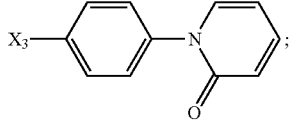

Subgenus IV wherein $X_3$ is selected from the group consisting of H, halogen, $C_1$-$C_{10}$ alkoxy, OH, $C_1$-$C_{10}$ alkyl, substituted $C_1$-$C_{10}$ alkyl, $C_1$-$C_{10}$ alkenyl, haloalkyl, nitroalkyl, $C_1$-$C_{10}$ thioalkyl, $C_1$-$C_{10}$ hydroxyalkyl, phenyl, substituted phenyl, $C_1$-$C_{10}$ alkoxyalkyl, $C_1$-$C_{10}$ carboxy, $C_1$-$C_{10}$ alkoxycarbonyl, CO-uronide, CO-monosaccharide, CO-oligosaccharide, and CO-polysaccharide.

Another embodiment provides a family of compounds represented by the following subgenus (Subgenus V):

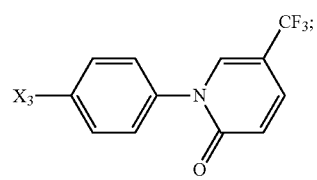

Subgenus V wherein $X_3$ is selected from the group consisting of H, halogen, $C_1$-$C_{10}$ alkoxy, $C_1$-$C_{10}$ alkyl, substituted $C_1$-$C_{10}$ alkyl, $C_1$-$C_{10}$ alkenyl, $C_1$-$C_{10}$ haloalkyl, $C_1$-$C_{10}$ nitroalkyl, $C_1$-$C_{10}$ thioalkyl, $C_1$-$C_{10}$ hydroxyalkyl, phenyl, substituted phenyl, $C_1$-$C_{10}$ alkoxyalkyl, $C_1$-$C_{10}$ carboxy, $C_1$-$C_{10}$ alkoxycarbonyl, CO-uronide, CO-monosaccharide, CO-oligosaccharide, and CO-polysaccharide.

Another embodiment provides a family of compounds represented by the following genus (Genus VI):

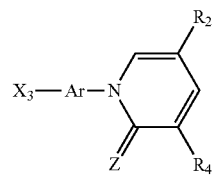

Genus VI wherein

Ar is pyridinyl or phenyl;

Z is O or S;

$X_3$ is H, F, Cl, OH, $CH_3$, or $OCH_3$;

$R_2$ is methyl, C(=O)H, C(=O)$CH_3$, C(=O)$OCH_3$, C(=O)O-glucosyl, fluoromethyl, difluoromethyl, trifluoromethyl, bromo, methylmethoxyl, methylhydroxyl, or phenyl; and $R_4$ is H or hydroxyl;

with the proviso that when $R_2$ is trifluoromethyl, Z is O, $R_4$ is H and Ar is phenyl, the phenyl is not solely substituted at the 4' position by H, F, or OH.

The Genus VI includes the families of compounds represented by the Subgenus VIa and the Subgenus VIb:

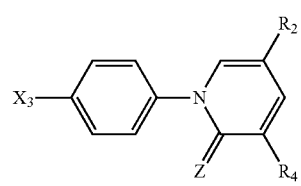

Subgenus VIa

-continued

Subgenus VIb

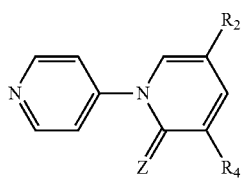

wherein Z, $X_3$, $R_2$ and $R_4$ are defined as in Genus VI. It will be recognized that the phenyl ring in the structure represented by Subgenus VIa is substituted by $X_3$ at the 4' position.

Another embodiment provides a family of compounds represented by the following genus (Genus VII):

Genus VII

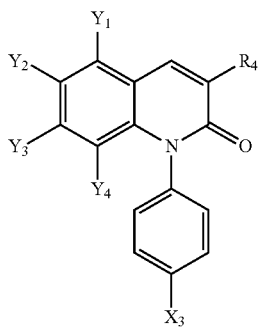

wherein $X_3$ is selected from the group consisting of H, halogen, $C_1$-$C_{10}$ alkoxy, and OH;

$Y_1$, $Y_2$, $Y_3$, and $Y_4$ are independently selected from the group consisting of H, $C_1$-$C_{10}$ alkyl, substituted $C_1$-$C_{10}$ alkyl, $C_1$-$C_{10}$ alkenyl, $C_1$-$C_{10}$ haloalkyl, $C_1$-$C_{10}$ nitroalkyl, $C_1$-$C_{10}$ thioalkyl, $C_1$-$C_{10}$ hydroxyalkyl, $C_1$-$C_{10}$ alkoxy, phenyl, substituted phenyl, halogen, hydroxyl, $C_1$-$C_{10}$ alkoxyalkyl, $C_1$-$C_{10}$ carboxy, $C_1$-$C_{10}$ alkoxycarbonyl; and $R_4$ is selected from the group consisting of H, halogen, and OH.

It will be recognized that a particular compound described herein may be a member of more than one of the various genera described above. The compounds described herein are useful for modulating a stress activated protein kinase (SAPK) system. Exemplary compounds of Genera Ia-c, Subgenera II-V and Genera VI and VII that are useful for modulating a stress activated protein kinase (SAPK) system are set forth in Table 1 below. Compounds 1-6 are examples of compounds of Subgenus II. Compounds 7-12 are examples of compounds of Subgenus III. Compound 13 is pirfenidone, an example of a compound of Subgenus II. Compounds 14-32 are examples of compounds of Genus VI. Compound 33 is an example of Genus VII.

TABLE 1

| Compound Number | Compound |
|---|---|
| 1 | ![Compound 1] |
| 2 | ![Compound 2] |
| 3 | ![Compound 3] |
| 4 | ![Compound 4] |
| 5 | ![Compound 5] |
| 6 | ![Compound 6] |
| 7 | ![Compound 7] |
| 8 | ![Compound 8] |

TABLE 1-continued

| Compound Number | Compound |
|---|---|
| 9 | 1-(4-hydroxyphenyl)pyridin-2(1H)-one |
| 10 | 1-(4-hydroxyphenyl)-5-(trifluoromethyl)pyridin-2(1H)-one |
| 11 | 1-(4-fluorophenyl)pyridin-2(1H)-one |
| 12 | 1-(4-fluorophenyl)-5-(trifluoromethyl)pyridin-2(1H)-one |
| 13 | 5-methyl-1-phenylpyridin-2(1H)-one |
| 14 | 1-(4-fluorophenyl)-5-methylpyridin-2(1H)-one |
| 15 | 1-(4-methoxyphenyl)-5-(trifluoromethyl)pyridin-2(1H)-one |
| 16 | 5-acetyl-1-phenylpyridin-2(1H)-one |
| 17 | 1,5-diphenylpyridin-2(1H)-one |
| 18 | 5-methyl-1-phenylpyridine-2(1H)-thione |
| 19 | 5-(difluoromethyl)-1-phenylpyridin-2(1H)-one |
| 20 | 6-oxo-1-phenyl-1,6-dihydropyridine-3-carbaldehyde |
| 21 | 1-(4-chlorophenyl)-5-(trifluoromethyl)pyridin-2(1H)-one |
| 22 | 5-methyl-1-(pyridin-3-yl)pyridin-2(1H)-one |
| 23 | 5-(fluoromethyl)-1-phenylpyridin-2(1H)-one |

TABLE 1-continued

| Compound Number | Compound |
|---|---|
| 24 | methyl 6-oxo-1-phenyl-1,6-dihydropyridine-3-carboxylate |
| 25 | 5-methyl-1-(1-methylpyridin-1-ium-4-yl)pyridin-2(1H)-one |
| 26 | 5-bromo-1-phenylpyridin-2(1H)-one |
| 27 | 5-bromo-1-(4-methoxyphenyl)pyridin-2(1H)-one |
| 28 | 5-(fluoromethyl)-1-(4-hydroxyphenyl)pyridin-2(1H)-one |
| 29 | 5-(difluoromethyl)-1-(4-hydroxyphenyl)pyridin-2(1H)-one |
| 30 | 5-bromo-1-(4-hydroxyphenyl)pyridin-2(1H)-one |
| 31 | 5-(fluoromethyl)-1-(4-methoxyphenyl)pyridin-2(1H)-one |
| 32 | 5-(difluoromethyl)-1-(4-methoxyphenyl)pyridin-2(1H)-one |
| 33 | 6-bromo-1-phenylquinolin-2(1H)-one |

Another embodiment is directed to purified compounds represented by Genera Ia-c, Subgenera II-V and/or Genera VI and VII. The degree of purity may be expressed as a percentage as described above. In preferred embodiments, purified compounds represented by Genera Ia-c, Subgenera II-V and/or Genera VI and VII have a purity of about 96% or greater, more preferably about 98% or greater, by weight based on total weight of the composition that comprises the purified compound. For example, an embodiment provides purified Compound 3 (Table 1).

Compounds of Genera Ia-c, Subgenera II-V and/or Genera VI and VII can be synthesized by using various reactions. Examples of syntheses include the following, designated Synthetic Schemes 1, 2, and 3.

Synthetic Scheme 1

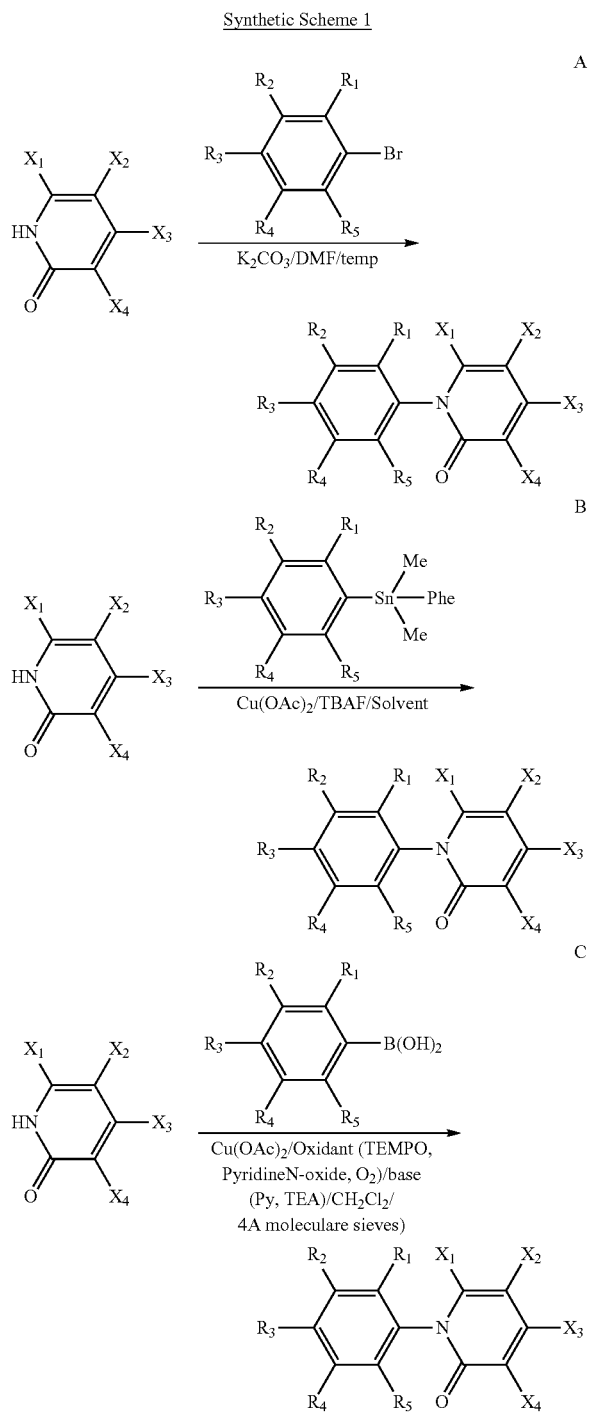

$X_1 = X_2 = X_3 = X_4 =$ H, alkyl, alkenyl, nitroalkyl, thioalkyl, phenyl, substituted phenyl, $CH_2Phe$, halogen, hydroxy, alkoxy, haloalkyl
$R_1 = R_2 = R_3 = R_4 = R_5 =$ H, alkyl, alkenyl, nitroalkyl, thioalkyl, phenyl, substituted phenyl, $CH_2Phe$, halogen, hydroxy, alkoxy, haloalkyl Synthetic Scheme 2

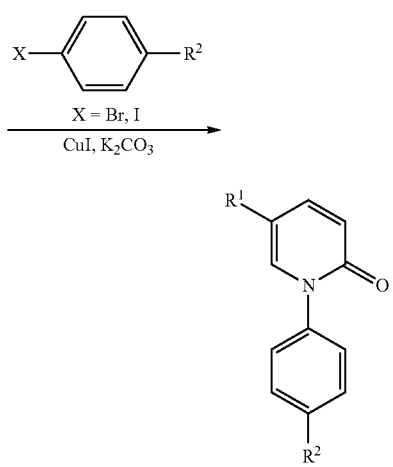

Ullmann reaction: Chem. Pharm. Bull. 45(4) 719-721. Target N-aryl-pyridine-2-ones were obtained via arylation of 2-hydroxypyridines. The Ullmann reaction is useful in the preparation of disclosed compounds, except the 5-bromo analogs and compound 33 which are afforded, for example, by synthetic scheme 3.

A mixture of 2-hydroxypyridine (1 mmol), aryl iodide or bromide (2 mmol), CuI (0.1-0.5 mmol) and anhydrous potassium carbonate (1 mmol) in DMF (3 ml) was stirred overnight at 135° C. under argon atmosphere. Deep colored reaction mixture was taken into ethyl acetate and 10% ammonium hydroxide. Organic layer was washed with brine and dried over magnesium sulfate. Column chromatography furnished target compounds as off-white solids in 25-60% yield.

Synthetic Scheme 3

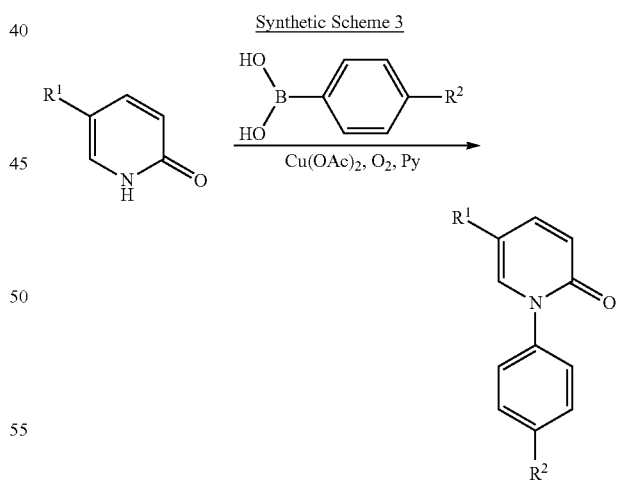

Target N-aryl-2-pyridones may be obtained via arylation of 2-hydroxypyridines with alkylboronic acids (*Tetrahedron Lett.*, 42 (2001) 3415-3418). The alkylboronic acid route is useful in the preparation of disclosed compounds. A mixture of 2-hydroxypyridine (5 mmol), arylboronic acid (10 mmol), cupper(II) acetate (0.5-1 mmol), pyridine (10 mmol) and molecular sieves 4A (0.5-1 g) in dichloromethane (25 ml) was stirred for 24-48 hours at room temperature opened to the air. Reaction mixture was washed with saturated sodium bicarbonate with EDTA and organic phase was dried over sodium sulfate. Target N-aryl-2-pyridones were isolated by column chromatography as white solids in 85-100% yield.

As pirfenidone derivatives, compounds of Genera Ia-c, Subgenera II-V and/or Genera VI and VII may also be synthesized by any conventional reactions known in the art based on the known synthetic schemes for pirfenidone, such as disclosed in U.S. Pat. Nos. 3,839,346; 3,974,281; 4,042,699; and 4,052,509, all of which are hereby expressly incorporated by reference in their entirety.

Starting materials described herein are available commercially, are known, or can be prepared by methods known in the art. Additionally, starting materials not described herein are available commercially, are known, or can be prepared by methods known in the art.

Starting materials can have the appropriate substituents to ultimately give desired products with the corresponding substituents. Alternatively, substituents can be added at any point of synthesis to ultimately give desired products with the corresponding substituents.

Synthetic Schemes 1-3 show methods that can be used to prepare compounds of Genera Ia-c, Subgenera II-V and/or Genera VI and VII. One skilled in the art will appreciate that a number of different synthetic reaction schemes can be used to synthesize the compounds of Genera Ia-c, Subgenera II-V and/or Genera VI and VII. Further, one skilled in the art will understand that a number of different solvents, coupling agents, and reaction conditions can be used in the syntheses reactions to yield comparable results.

One skilled in the art will appreciate variations in the sequence and, further, will recognize variations in the appropriate reaction conditions from the analogous reactions shown or otherwise known which may be appropriately used in the processes above to make the compounds of Genera Ia-c, Subgenera II-V and/or Genera VI and VII.

In the processes described herein for the preparation of the compounds of compounds of Genera Ia-c, Subgenera II-V and/or Genera VI and VII, the use of protective groups is generally well recognized by one skilled in the art of organic chemistry, and accordingly the use of appropriate protecting groups may in some cases be implied by the processes of the schemes herein, although such groups may not be expressly illustrated. Introduction and removal of such suitable protecting groups are well known in the art of organic chemistry; see for example, T. W. Greene, "Protective Groups in Organic Synthesis", Wiley (New York), 1999. The products of the reactions described herein may be isolated by conventional means such as extraction, distillation, chromatography, and the like.

The salts, e.g., pharmaceutically acceptable salts, of the compounds of Genera Ia-c, Subgenera II-V and/or Genera VI and VII may be prepared by reacting the appropriate base or acid with a stoichiometric equivalent of the compounds. Similarly, pharmaceutically acceptable derivatives (e.g., esters), metabolites, hydrates, solvates and prodrugs of the compounds of Genera Ia-c, Subgenera II-V and/or Genera VI and VII may be prepared by methods generally known to those skilled in the art. Thus, another embodiment provides compounds that are prodrugs of an active compound. In general, a prodrug is a compound which is metabolized in vivo (e.g., by a metabolic transformation such as deamination, dealkylation, de-esterification, and the like) to provide an active compound. A "pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of the compounds of the embodiments. Examples of pharmaceutically-acceptable prodrug types are described in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are hereby expressly incorporated by reference in their entirety.

The compounds and compositions described herein may also include metabolites. As used herein, the term "metabolite" means a product of metabolism of a compound of the embodiments or a pharmaceutically acceptable salt, analog, or derivative thereof, that exhibits a similar activity in vitro or in vivo to a compound of the embodiments. The compounds and compositions described herein may also include hydrates and solvates. As used herein, the term "solvate" refers to a complex formed by a solute (herein, a compound of Genera Ia-c, Subgenera II-V and/or Genera VI and VII) and a solvent. Such solvents for the purpose of the embodiments preferably should not interfere with the biological activity of the solute. Solvents may be, by way of example, water, ethanol, or acetic acid. In view of the foregoing, reference herein to a particular compound or genus of compounds will be understood to include the various forms described above, including pharmaceutically acceptable salts, esters, prodrugs, metabolites and solvates thereof unless stated otherwise.

Methods of Inhibiting p38 MAP Kinase

In an embodiment, methods are provided for modulating a SAPK system, in vitro or in vivo. The methods include contacting a SAPK-modulating concentration of a compound with at least one p38 MAPK (e.g., by contacting the compound with a cell or tissue containing at least one p38 MAPK), where the compound has a relatively low potency for inhibition of the at least one p38 MAPK, corresponding to a relatively high inhibitory concentration for inhibition of the at least one p38 MAPK by the compound.

"Contacting a cell" refers to a condition in which a compound or other composition of matter is in direct contact with a cell or tissue, or is close enough to induce a desired biological effect in a cell or tissue. For example, contacting a cell or tissue containing p38 MAPK with a compound may be conducted in any manner that permits an interaction between p38 MAPK and the compound, resulting in the desired biological effect in a cell. Contacting a cell or tissue may be accomplished, for example, by intermixing or administration of a compound (such as a compound of Genera Ia-c, Subgenera II-V and/or Genera VI and VII and/or a salt, ester, prodrug and/or intermediate thereof, and/or a pharmaceutical composition comprising one or more of the foregoing).

Alternatively, contacting a cell or tissue may be accomplished by introducing a compound in a manner such that the compound will be targeted, directly or indirectly, to a cell or tissue containing p38 MAPK. Contacting a cell or tissue may be accomplished under conditions such that a compound binds to at least one p38 MAPK. Such conditions may include proximity of the compound and p38-containing cell or tissue, pH, temperature, or any condition that affects the binding of a compound to p38 MAPK.

In certain embodiments, the cell is contacted with the compound in vitro; in other embodiments, the cell is contacted with the compound in vivo.

When the cell is contacted in vivo, the effective concentration (EC) of a compound is a concentration that results in a reduction of a specified endpoint by a target percentage (e.g., 50%, 40%, 30%, 20%, 10%) relative to the maximal observable reduction of the specified endpoint by that compound. Such an endpoint may be a physiological response, for example, reduction in blood or other bodily fluid concentration of TNFα. For example, $EC_{50}$, $EC_{40}$, $EC_{30}$, $EC_{20}$ and $EC_{10}$ are determined as concentrations that result in reductions in the serum TNFα concentration by 50%, 40%, 30%, 20% and 10%, respectively, relative to the maximal observable reduction on a dose-response curve.

When the cell is contacted in vitro, except in a cell-based assay, the effective concentration (EC) is a concentration that results in a reduction in the activity of the specified target by a given percentage (e.g., 50%, 40%, 30%, 20%, 10%). For example, $EC_{50}$, $EC_{40}$, $EC_{30}$, $EC_{20}$ and $EC_{10}$ are determined as concentrations that result in reductions in the activity of the specified target by 50%, 40%, 30%, 20% and 10%, respectively, on a dose-response curve. When complete inhibition of a specified target is not obtained, the effective concentration (EC) of a compound is a concentration that results in a reduction of a target activity by a given percentage (e.g., 50%, 40%, 30%, 20%, 10%) relative to the maximal reduction of the target activity by that compound.

When the cell is contacted in vitro, in a cell-based assay, the effective concentration (EC) of a compound is a concentration that results in a reduction of a specified endpoint by a target percentage (e.g., 50%, 40%, 30%, 20%, 10%) relative to the maximal observable reduction of the specified endpoint by that compound. Such an endpoint may be a cellular response, for example, reduction in the secretion of TNFα as determined by the TNFα concentration in cell medium. For example, $EC_{50}$, $EC_{40}$, $EC_{30}$, $EC_{20}$ and $EC_{10}$ are determined as concentrations that result in reductions in the TNFα concentration by 50%, 40%, 30%, 20% and 10%, respectively, relative to the maximal observable reduction on a dose-response curve.

The $EC_{50}$ of the SAPK system-modulating compound is preferably in the range of about 1 µM to about 1000 µM, more preferably about 50 µM to about 650 µM for inhibition of at least one p38 MAPK. Thus, for example, modulation of the SAPK system may involve contacting a compound (e.g., a compound of Genera Ia-c, Subgenera II-V and/or Genera VI and VII) with at least one p38 MAPK at a concentration that is less than an $EC_{40}$, preferably less than $EC_{30}$, more preferably less than $EC_{20}$, even preferably less than $EC_{10}$ for inhibition of the at least one p38 MAPK by the compound as determined on a dose-response curve in vivo.

In certain embodiments, the compound is provided in the form of a pharmaceutical composition, together with a pharmaceutically acceptable carrier.

Screening a Library of Compounds for Low-Potency p38 Inhibitors

In another aspect, a method is provided for identifying a pharmaceutically active compound, e.g., for determining whether a compound is potentially useful as a therapeutic agent, e.g., for the prevention or treatment of an inflammatory condition (such as p38- or cytokine-associated condition). The method includes assaying a plurality of compounds for inhibition of at least one p38 MAPK and selecting a compound which exhibits a relatively low potency for inhibiting p38 MAPK. Preferably, an $EC_{50}$ of such a low-potency p38 inhibitor compound is in the range of about 1 µM to about 1000 µM, preferably about 50 µM to about 650 µM for inhibition of the at least one p38 MAPK. The plurality of compounds to be assayed is preferably selected from a library of potential compounds. The assaying of the plurality of compounds from the library may be conducted in various ways. For example, in some embodiments, the methods further comprise contacting at least one p38 MAPK with the plurality of compounds, and determining whether the compounds inhibit the activity of cytokines. A p38 MAPK is preferably selected from the group consisting of p38α, p38β, p38γ, and p38δ. In preferred embodiments, the contacting step takes place in vitro; in certain preferred embodiments, the contacting step comprises contacting a cell comprising p38 MAPK with the compound.

In yet another embodiment, methods are provided for inhibiting the activity of p38 MAPK in a cell, in vitro or in vivo. In general, such methods include contacting a cell containing at least one p38 MAPK with an effective p38-inhibiting amount of a compound (e.g., a compound of Genera Ia-c, Subgenera II-V and/or Genera VI and VII), under conditions such that p38 activity in the cell is inhibited. Examples of such methods are provided in the EXAMPLES section below. The compound preferably exhibits an $EC_{50}$ in the range of about 1 µM to about 1000 µM, preferably about 50 µM to about 650 µM for inhibition of the at least one p38 MAPK. The contacting of at least one p38 MAPK with the compound is preferably conducted at a SAPK system-modulating concentration that is less than $EC_{30}$, preferably less than $EC_{20}$, more preferably less than $EC_{10}$ for inhibition of the at least one p38 MAPK by the compound.

In vivo methods include for example, introducing into a group of animals orally or by injection a compound of interest (e.g., a compound of Genera Ia-c, Subgenera II-V and/or Genera VI and VII) in various concentrations. Following the introduction of the compound, lipopolysaccharide is administered intravenously. Serum TNFα levels are measured and compared to that from control animals. The preferred compounds inhibit the release of TNFα, thus reducing TNFα levels in the blood samples of the tested animals. The compound preferably exhibits an $EC_{50}$ in the range of about 1 µM to about 1000 µM, preferably about 50 µM to about 650 µM for inhibition of the release of TNFα.

The method of identifying a pharmaceutically active compound may further include determining a mammalian toxicity of the selected compound. Such methods are generally known to those skilled in the art. The method of identifying a pharmaceutically active compound may also include administering the selected compound to a test subject, either in conjunction with the determination of mammalian toxicity or for other reasons. In an embodiment, the test subject test subject has or is at risk for having an inflammatory condition. Preferably the test subject is a mammal, and may be a human.

Methods of Treatment and/or Prevention

Another embodiment provides methods for treating or preventing disease states, e.g., inflammatory condition(s) and/or fibrotic condition(s). The methods include identifying a subject at risk for or having at least one condition selected from an inflammatory condition and a fibrotic condition and administering a compound to the subject in an effective amount to treat or prevent the inflammatory condition and/or fibrotic condition. In preferred embodiments, the compound exhibits an $EC_{50}$ in the range of about 1 µM to about 1000 µM, preferably about 50 µM to about 650 µM for inhibition of at least one p38 MAPK. In preferred embodiments, the effective amount produces a blood or serum or another bodily fluid concentration that is less than an $EC_{30}$ or, preferably, an $EC_{20}$ or, more preferably, an $EC_{10}$ for inhibition of p38 MAPK by the compound. In preferred embodiments, the compound exhibits an $EC_{50}$ in the range of about 1 µM to about 1000 µM, preferably about 50 µM to about 650 µM for inhibition of the TNFα secretion. In other preferred embodiments, the effective amount produces a blood or serum or another bodily fluid concentration that is less than an $EC_{30}$ or, preferably, an $EC_{20}$ or, more preferably, an $EC_{15}$ or, more preferably, an $EC_{10}$ for inhibition of LPS-stimulated TNFα release in a bodily fluid by the compound. The effective amount is preferably about 70% or less, more preferably less than about 50%, of an amount that causes an undesirable side effect in the subject, such as, but not limited to, drowsiness, nausea, cold symptom, gastrointestinal upset, and photosensitivity rash. The compound used for the treatment or prevention is preferably a compound of Genera Ia-c, Subgenera II-V and/or Genera VI and VII.

Methods for identifying a subject at risk for or having an inflammatory condition are known to those skilled in the art. Examples of inflammatory conditions that may be treated or prevented by the methods described herein include p-38 associated conditions, e.g., conditions associated with altered cytokine activity, conditions associated with modulation of an SAPK system, autoimmune diseases, and diseases associated with acute and chronic inflammation. The cytokine (or cytokines) is (are) preferably selected from the group consisting of, but not limited to, IL-1β, IL-6, IL-8, and TNFα. In an embodiment, the compound used to treat or prevent the inflammatory condition is compound that inhibits a kinase in the SAPK signaling pathway. Examples of preferred compounds include compound of Genera Ia-c, Subgenera II-V and/or Genera VI and VII.

The term "p38-associated condition" means a disease or other deleterious condition in which the p38 MAP kinase signaling pathway is implicated, whether directly or indirectly. Examples of p38-associated conditions include conditions caused by IL-1β, TNFα, IL-6 or IL-8 dysregulation or overexpression resulting from sustained, prolonged, enhanced or elevated levels of p38 activity. Such conditions include, without limitation, inflammatory diseases, autoimmune diseases, fibrotic diseases, destructive bone disorders, proliferative disorders, infectious diseases, neurodegenerative diseases, allergies, reperfusion ischemia in stroke, heart attacks, angiogenic disorders, organ hypoxia, vascular hyperplasia, cardiac hypertrophy, thrombin-induced platelet aggregation, and conditions associated with the prostaglandin or cyclooxygenase pathways, e.g., conditions involving prostaglandin endoperoxide synthase. A p38-associated condition can include any condition associated with or mediated by an isoform of p38.

A "fibrotic condition," "fibroproliferative condition," "fibrotic disease," "fibroproliferative disease," "fibrotic disorder," and "fibroproliferative disorder" are used interchangeably to refer to a condition, disease or disorder that is characterized by dysregulated proliferation or activity of fibroblasts and/or pathologic or excessive accumulation of collagenous tissue. Typically, any such disease, disorder or condition is amenable to treatment by administration of a compound having anti-fibrotic activity. Fibrotic disorders include, but are not limited to, pulmonary fibrosis, including idiopathic pulmonary fibrosis (IPF) and pulmonary fibrosis from a known etiology, liver fibrosis, and renal fibrosis. Other exemplary fibrotic conditions include musculoskeletal fibrosis, cardiac fibrosis, post-surgical adhesions, scleroderma, glaucoma, and skin lesions such as keloids.

The term "modulating SAPK system" means increasing or decreasing activity of the stress-activated protein kinase system activity, e.g., by inhibiting p38 activity, whether in vitro or in vivo. In certain embodiments, the SAPK system is modulated when p38 activity in a cell is inhibited by about 50%, preferably by about 40%, more preferably by about 30%, even more preferably by about 20%, or yet even more preferably by about 10% compared to the p38 activity of an untreated control cell.

A condition associated with altered cytokine activity, as used herein, refers to a condition in which cytokine activity is altered compared to a non-diseased state. This includes, but is not limited to, conditions caused by IL-1β, TNFα, IL-6 or IL-8 overproduction or dysregulation resulting in sustained, prolonged, enhanced or elevated levels of cytokine activity, which may be associated with p38 activity. Such conditions include, without limitation, inflammatory diseases, autoimmune diseases, fibrotic diseases, destructive bone disorders, proliferative disorders, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with the cyclooxygenase and lipoxygenase signaling pathways, such as prostaglandin endoperoxide synthase. A cytokine-associated condition can include any condition associated with or mediated by IL-1 (particularly IL-1β), TNFα, IL-6 or IL-8, or any other cytokine which can be regulated by p38. In preferred embodiments, the cytokine associated condition is a condition associated with TNFα.

The methods described herein may also be used to treat autoimmune diseases and diseases associated with acute and chronic inflammation. These diseases include, but are not limited to: chronic obstructive pulmonary disease (COPD), bronchiolitis obliterans syndrome, chronic allograft fibrosis, inflammatory pulmonary fibrosis (IPF), rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute and chronic renal disease; renal fibrosis, irritable bowel syndrome; pyresis; restenosis; cerebral malaria; stroke and ischemic injury; neural trauma; Alzheimer's disease; Huntington's disease; Parkinson's disease; acute and chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as Multiple Sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the embodiments can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal. carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation. In addition, the methods described herein may be useful for the treatment of protozoal diseases in animals, including mammals.

A subject may include one or more cells or tissues, or organisms. A preferred subject is a mammal. A mammal may include any mammal. As a non-limiting example, preferred mammals include cattle, pigs, sheep, goats, horses, camels, buffalo, cats, dogs, rats, mice, and humans. A highly preferred subject mammal is a human. The compound(s) may be administered to the subject via any drug delivery route known in the art. Specific exemplary administration routes include oral, ocular, rectal, buccal, topical, nasal, ophthalmic, subcutaneous, intramuscular, intravenous (bolus and infusion), intracerebral, transdermal, and pulmonary.

The terms "therapeutically effective amount" and "prophylactically effective amount", as used herein, refer to an amount of a compound sufficient to treat, ameliorate, or prevent the identified disease or condition, or to exhibit a detectable therapeutic, prophylactic, or inhibitory effect. The effect can be detected by, for example, the assays disclosed in the following examples. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician. Preferably, the effective amount of the compound of the embodiments produces a blood or serum or another bodily fluid concentration that is less than an $EC_{30}$, $EC_{20}$ or $EC_{10}$ for inhibition of p38 MAP kinase.

For any compound, the therapeutically or prophylactically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans.

Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. However, the pharmaceutical compositions that exhibit narrow therapeutic indices are also within the scope of the embodiments. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the maximum plasma concentrations ($C_{max}$) may range from about 65 µM to about 115 µM, or about 75 µM to about 105 µM, or about 85 µM to about 95 µM, or about 85 µM to about 90 µM depending upon the route of administration. Guidance as to particular dosages and methods of delivery is provided in the literature and is generally available to practitioners in the art. In general the dose will be in the range of about 100 mg/day to about 10 g/day, or about 200 mg to about 5 g/day, or about 400 mg to about 3 g/day, or about 500 mg to about 2 g/day, in single, divided, or continuous doses for a patient weighing between about 40 to about 100 kg (which dose may be adjusted for patients above or below this weight range, particularly children under 40 kg). Generally the dose will be in the range of about 25 mg/kg to about 300 mg/kg of body weight per day.

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered twice a day, once a day, once very two days, three times a week, twice a week, every 3 to 4 days, or every week depending on half-life and clearance rate of the particular formulation. For example, in an embodiment, a pharmaceutical composition contains an amount of a compound as described herein that is selected for administration to a patient on a schedule selected from: twice a day, once a day, once very two days, three times a week, twice a week, and once a week.

It will be appreciated that treatment as described herein includes preventing a disease, ameliorating symptoms, slowing disease progression, reversing damage, or curing a disease.

In one aspect, treating an inflammatory condition results in an increase in average survival time of a population of treated subjects in comparison to a population of untreated subjects. Preferably, the average survival time is increased by more than about 30 days; more preferably, by more than about 60 days; more preferably, by more than about 90 days; and even more preferably by more than about 120 days. An increase in survival time of a population may be measured by any reproducible means. In a preferred aspect, an increase in average survival time of a population may be measured, for example, by calculating for a population the average length of survival following initiation of treatment with an active compound. In an another preferred aspect, an increase in average survival time of a population may also be measured, for example, by calculating for a population the average length of survival following completion of a first round of treatment with an active compound.

In another aspect, treating an inflammatory condition results in a decrease in the mortality rate of a population of treated subjects in comparison to a population of subjects receiving carrier alone. In another aspect, treating an inflammatory condition results in a decrease in the mortality rate of a population of treated subjects in comparison to an untreated population. In a further aspect, treating an inflammatory condition results a decrease in the mortality rate of a population of treated subjects in comparison to a population receiving monotherapy with a drug that is not a compound of the embodiments, or a pharmaceutically acceptable salt, metabolite, analog or derivative thereof. Preferably, the mortality rate is decreased by more than about 2%; more preferably, by more than about 5%; more preferably, by more than about 10%; and most preferably, by more than about 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease related deaths per unit time following completion of a first round of treatment with an active compound.

In another aspect, treating an inflammatory condition results in a decrease in growth rate of a tumor. Preferably, after treatment, tumor growth rate is reduced by at least about 5% relative to /number prior to treatment; more preferably, tumor growth rate is reduced by at least about 10%; more preferably, reduced by at least about 20%; more preferably, reduced by at least about 30%; more preferably, reduced by at least about 40%; more preferably, reduced by at least about 50%; even more preferably, reduced by at least 60%; and most preferably, reduced by at least about 75%. Tumor growth rate may be measured by any reproducible means of measurement. In a preferred aspect, tumor growth rate is measured according to a change in tumor diameter per unit time.

In another aspect, treating an inflammatory condition results in a reduction in the rate of cellular proliferation. Preferably, after treatment, the rate of cellular proliferation is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating an inflammatory condition results in a reduction in the proportion of proliferating cells. Preferably, after treatment, the proportion of proliferating cells is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating an inflammatory condition results in a decrease in size of an area or zone of cellular proliferation. Preferably, after treatment, size of an area or zone of cellular proliferation is reduced by at least 5% relative to its size prior to treatment; more preferably, reduced by at least about 10%; more preferably, reduced by at least about 20%; more preferably, reduced by at least about 30%; more preferably, reduced by at least about 40%; more preferably, reduced by at least about 50%; even more preferably, reduced by at least about 60%; and most preferably, reduced by at least about 75%. Size of an area or zone of cellular proliferation may be measured by any reproducible means of measurement. In a preferred aspect, size of an area or zone of cellular proliferation may be measured as a diameter or width of an area or zone of cellular proliferation.

The methods described herein may include identifying a subject in need of treatment. In a preferred embodiment, the methods include identifying a mammal in need of treatment. In a highly preferred embodiment, the methods include identifying a human in need of treatment. Identifying a subject in need of treatment may be accomplished by any means that indicates a subject who may benefit from treatment. For example, identifying a subject in need of treatment may occur by clinical diagnosis, laboratory testing, or any other means known to one of skill in the art, including any combination of means for identification.

As described elsewhere herein, the compounds described herein may be formulated in pharmaceutical compositions, if desired, and can be administered by any route that permits treatment of the disease or condition. A preferred route of administration is oral administration. Administration may take the form of single dose administration, or the compound of the embodiments can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

The methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Diagnostic tests are contemplated as part of the methods described herein. For example, a tissue biopsy sample may be taken from a subject suffering from an inflammatory condition, e.g., a p38-associated or cytokine-associated condition. The biopsy sample can be tested to determine the level of p38 activity (or cytokine levels) present in the sample; the sample can then be contacted with a selected compound of the embodiments, and the p38 activity (or cytokine levels) measured to determine whether the compound has a desired effect (e.g., inhibition of p38 or cytokine activity with an $EC_{50}$ in the range of about 100 µM and about 1000 µM, preferably about 50 µM to about 650 µM). Such a test may be used to determine whether treatment with such a compound is likely to be effective in that subject. Alternatively, the sample may be contacted with a labeled compound (e.g., a fluorescently-labeled compound, or a radioactivity-labeled compound) and the sample then examined and the fluorescent or radioactive signal detected to determine the distribution of p38 in the tissue sample. Repeated biopsy samples taken during a course of treatment may also be used to study the efficacy of the treatment. Other diagnostic tests using the compounds described herein will be apparent to one of ordinary skill in the art in light of the teachings of this specification.

Thus, for example, an embodiment provides methods for determining the presence, location, or quantity, or any combination thereof of p38 protein in a cell or tissue sample. The methods include: a) contacting the cell or tissue sample with a compound of the embodiments under conditions such that the compound can bind to at least one p38 MAPK; and b) determining the presence, location, or quantity, or any combination thereof of the compound in the cell or tissue sample, thereby determining the presence, location, or quantity, or any combination thereof of the at least one p38 MAPK in the cell or tissue sample. Determining the presence, location, or quantity, or any combination thereof of the compound in the cell or tissue sample may be conducted by any means that reveals the presence, location, or quantity, or any combination thereof of the compound in the cell or tissue. For example, as described previously, radioactive or fluorescent labeling methods may be used. Additional methods of determining the presence, location, or quantity, or any combination thereof of the compound will be apparent to a skilled artisan.

Another embodiment provides methods for determining: (1) whether a compound will be a useful therapeutic agent for treatment of a subject suffering from an inflammatory condition, or (2) the severity of disease or (3) the course of disease during treatment with a disease-modifying agent. The methods include: a) obtaining a cell or tissue sample from the subject before, during and after termination of treatment with a compound as described herein or another disease-modifying agent; b) contacting the sample with the compound; and c) determining the amount of the compound that binds to the sample, wherein binding to p38 MAPK by the compound is related to the amount of p38 MAPK in the sample.

Specific Examples of Diseases Contemplated to be Treated by the Compounds and Methods Described Herein

COPD

Chronic obstructive pulmonary disease (COPD) is characterized by a chronic inflammatory process in the lung that includes (1) increased number of inflammatory cells (neutrophils, macrophages and SD8$^+$ T cells) in the airways and parenchyma, (2) increased inflammatory cytokine and chemokine expression, and (3) increased number of proteases (elastases, cathepsins, and matrix metalloproteinases, MMPs). The production and action of many of potential mediators of airway inflammation are believed to be dependent on the stress-induced MAPK or p38 kinase cascade. Several reports support the association pf p38 kinase activation with as plethora of pulmonary events: LPS- and TNF-α-induced intercellular adhesion molecule-1 expression on pulmonary microvascular endothelial cells, MMP-9 activation, hypoxia-induced stimulation of pulmonary arterial cells, hyperosmolarity-induced IL-8 expression in bronchial epithelial cells, and enhanced eosinophil trafficking and survival.

Trifilieff et al. (2005 *Brit J Pharmacol* 144:1002-10) reported that CGH2466, a combined adenosine receptor antagonist, p38 MAPK and phosphodiesterase type 4 inhibitor showed potent in vitro and in vivo anti-inflammatory activities in diseases such as asthma and COPD. Underwood et al. (2000 *Am J Physiol Lung Cell Mol Physiol* 279:L895-L902) demonstrated that the potent and selective p38 MAPK inhibitor, SB239063, reduced proinflammatory cytokine production, including IL-1β, TNF-α, IL-6, and IL-8, which have been linked to airway fibrosis because of their ability to regulate fibroblast proliferation and matrix production; that leads to diminished neutrophil trafficking and activation in the lung. Earlier, the same compound was found capable of altering responses associated with chronic fibrosis induced by bleomycin. This inhibitory activity was selective for the α and β isoforms of the p38. The compounds and methods described herein are useful in the treatment of COPD.

Pulmonary Fibrosis

Pulmonary fibrosis also called idiopathic pulmonary fibrosis (IPF), interstitial diffuse pulmonary fibrosis, inflammatory pulmonary fibrosis, or fibrosing alveolitis, is an inflammatory lung disorder and a heterogeneous group of conditions characterized by abnormal formation of fibrous tissue between alveoli caused by alveolitis comprising an inflammatory cellular infiltration into the alveolar septae with resulting fibrosis. The effects of IPF are chronic, progressive, and often fatal. p38 MAPK activation has been demonstrated in the lung of patients with pulmonary fibrosis. A number of investigations about pulmonary fibrosis have indicated that sustained and augmented expression of some cytokines in the lung are relevant to recruitment of inflammatory cells and accumulation of extracellular matrix components followed by remodeling of the lung architecture. In particular, proinflammatory cytokines such as TNF-α and interleukin IL-1β were demonstrated to play major roles in the formation of pneumonitis and pulmonary fibrosis. In addition, profibrotic cytokines such as TGF-β and CTGF also play critical roles in the pathogenesis of pulmonary fibrosis. Matsuoka et al. (2002 *Am J Physiol Lung Cell Mol Physiol* 283:L103-L112) have demonstrated that a p38 inhibitor, FR-167653, ameliorates murine bleomycin-induced pulmonary fibrosis. Furthermore, pirfenidone (5-methyl-1-phenyl-2-(1H)-pyridone), a compound with combined anti-inflammatory, antioxidant and antifibrotic effects was found effective in experimental models of pulmonary fibrosis as well as in clinical studies (Raghu et al. 1999 *Am J Respir Crit Care Med* 159:1061-1069; Nagai et al. 2002 *Intern Med* 41:1118-1123; Gahl et al. 2002 *Mol Genet Metab* 76:234-242; Azuma et al. 2002 *Am J Respir Crit Care Med* 165:A729). The compounds and methods described herein are useful in the treatment of pulmonary fibrosis, such as IPF.

Bronchiolitis Obliterans and Bronchiolitis Obliterans Syndrome

Bronchiolitis obliterans, and its correlating clinical condition bronchiolitis obliterans syndrome, are characterized by obstruction of the pulmonary pathway via obliteration of pulmonary small airways. In bronchiolitis obliterans, pathologic examination characteristically finds lesions which obstruct or obliterate small airways in the lung. These lesions are granular fibromyoid tissue and dense submucosal scar tissue. Lesions progress from prolonged, abnormal, or aberrant inflammation of epithelial and epithelial-localized structures of the small airways, mediated by proinflammatory cytokines such as TNF-α and result in excessive fibroproliferation. The obliteration of pulmonary small airways progressively leads to airflow obstruction, characterized by progressive decline in forced expiratory volume in one second ($FEV_1$), and is often accompanied by recurring infections of the lower respiratory tract and colonization of pulmonary tissue by pathogenic microorganisms.

Bronchiolitis obliterans syndrome affects 50-60% of patients surviving five years after lung transplantation surgery, and five year survival after onset of bronchiolitis obliterans syndrome is only 30-40%. Lung transplantation patients experiencing bronchiolitis obliterans syndrome often respond poorly to augmented immunosuppression. In patients with idiopathic pulmonary fibrosis, survival after bronchiolitis obliterans syndrome is shorter than in patients with emphysema. The compounds and methods described herein are useful in the treatment of bronchiolitis obliterans syndrome.

Chronic Allograft Fibrosis

Allograft failure is a profound concern in transplantation management. One of the primary causes of allograft failure is chronic allograft dysfunction. Hallmarks of chronic allograft dysfunction are chronic inflammation and chronic fibrosis, both of which are associated with the production of inflammatory cytokines and growth factors. Mediation of inflammatory cytokine and growth factors, particularly resulting in interruption of collagen and TGF production, is useful in the treatment of chronic allograft fibrosis. The term "chronic allograft fibrosis" as used herein is intended to encompass both chronic inflammation and chronic fibrosis associated with chronic allograft fibrosis. The compounds and methods described herein are useful in the treatment of chronic allograft fibrosis.

Renal Fibrosis

Irrespective of the nature of the initial insult, renal fibrosis is considered to be the common final pathway by which kidney disease progresses to end-stage renal failure. Stambe et al. (2004 *J Am Soc Nephrol* 15:370-379) tested an inhibitor of the active (phosphorylated) form of p38, NPC 31169, developed by Scios Inc. (San Francisco, Calif.) in a rat model of renal fibrosis, and reported a significant reduction in renal fibrosis assessed by interstitial volume, collagen IV deposition, and connective tissue growth mRNA levels. The compounds and methods described herein are useful in the treatment of renal fibrosis.

Leiomyoma

Uterine leiomyomas or fibroids are the most common pelvic tumors in women with no known long-term effective drug therapies available. Leiomyomas are characterized by increased cell proliferation and tissue fibrosis. Pirfenidone was tested on cell proliferation and collagen expression in cultured myometrial and leiomyoma smooth muscle cells, and was found to be an effective inhibitor of myometrial and leiomyoma cell proliferation (Lee et al. 1998 *J Clin Endocrinol Metab* 83:219-223). The compounds and methods described herein are useful in the treatment of leiomyomas.

Endomyocardial Fibrosis

Endomyocardial fibrosis (EMF) is a disorder characterized by the development of restrictive cardiomyopathy. EMF is sometimes considered part of a spectrum of a single disease process that includes Löffler endocarditis (nontropical eosinophilic endomyocardial fibrosis or fibroplastic parietal endocarditis with eosinophilia). In EMF, the underlying process produces patchy fibrosis of the endocardial surface of the heart, leading to reduced compliance and, ultimately, restrictive physiology as the endomyocardial surface becomes more generally involved. Endocardial fibrosis principally involves the inflow tracts of the right and left ventricles and may affect the atrioventricular valves, leading to tricuspid and mitral regurgitation. MAPK activation was shown to contribute to arrhythmogenic atrial structural remodeling in EMF. The compounds and methods described herein are useful in the treatment and/or prevention of endomyocardial fibrosis.

Other Inflammatory Diseases

Many autoimmune diseases and diseases associated with chronic inflammation, as well as acute responses, have been linked to activation of p38 MAP kinase and overexpression or dysregulation of inflammatory cytokines. These diseases include, but are not limited to: rheumatoid arthritis; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synoviitis; muscle degeneration, bursitis; tendonitis; tenosynovitis; herniated, ruptures, or prolapsed intervertebral disk syndrome; osteopetrosis; thrombosis; cancer; restenosis; silicosis; pulmonary sarcosis; bone resorption diseases, such as osteoporosis; graft-versus-host reaction; and auto-immune diseases, such as Multiple Sclerosis, lupus and fibromyalgia; AIDS and other viral diseases such as Herpes Zoster, Herpes Simplex I or II, influenza virus and cytomegalovirus; and diabetes mellitus.

Many studies have shown that reducing the activity of p38 MAP kinase, its upstream activators or its downstream effectors, either through genetic or chemical means, blunts the inflammatory response and prevents or minimizes tissue damage (see, e.g., English, et al. 2002 *Trends Pharmacol Sci* 23:40-45; and Dong et al. 2002 *Annu Rev Immunol* 20:55-72). Thus, inhibitors of p38 activity, which also inhibit excess or unregulated cytokine production and may inhibit more than a single pro-inflammatory cytokine, may be useful as anti-inflammatory agents and therapeutics. Furthermore, the large number of diseases associated with p38 MAP kinase-associated inflammatory responses indicates that there is a need for effective methods for treating these conditions.

Cardiovascular Disease.

Inflammation and leukocyte activation/infiltration play a major role in the initiation and progression of cardiovascular diseases including atherosclerosis and heart failure. Acute p38 mitogen-activated protein kinase (MAPK) pathway inhibition attenuates tissue damage and leukocyte accumulation in myocardial ischemia/reperfusion injury. The compounds and methods described herein are useful for treating cardiovascular disease.

Multiple Sclerosis.

Inflammation in the central nervous system occurs in diseases such as multiple sclerosis and leads to axon dysfunction and destruction. Both in vitro and in vivo observations have shown an important role for nitric oxide (NO) in mediating inflammatory axonopathy. p38 MAP kinase is activated by NO exposure and inhibition of p38 signalling was shown to lead to neuronal and axonal survival effects. OCM and IGF-1 reduced p38 activation in NO-exposed cortical neurons and improved axon survival in cultures exposed to NO, a process dependent on mitogen-activated protein kinase/extracellular signal-related kinase signalling. The compounds and methods described herein are useful for treating multiple sclerosis.

Primary Graft Nonfunction.

Nonspecific inflammation is associated with primary graft nonfunction (PNF). Inflammatory islet damage is mediated at least partially by pro-inflammatory cytokines, such as interleukin-1β (IL-1β) and tumor necrosis factor-α (TNF-α) produced by resident islet macrophages. The p38 pathway is known to be involved in cytokine production in the cells of the monocyte-macrophage lineage. Inhibition of the p38 pathway by a chemical p38 inhibitor, SB203580, suppresses IL-1β and TNF-α production in human islets exposed to lipopolysaccharide (LPS) and/or inflammatory cytokines. Although IL-1β is predominantly produced by resident macrophages, ductal cells and islet vascular endothelial cells were found to be another cellular source of IL-1β in isolated human islets. SB203580 also inhibited the expression of inducible nitric oxide synthase (iNOS) and cyclooxygenase-2 (COX-2) in the treated islets. Furthermore, human islets treated with SB203580 for 1 h prior to transplantation showed significantly improved graft function. The compounds and methods described herein are useful for improving graft survival in clinical islet transplantation.

Acute Renal Injury.

Cisplatin is an important chemotherapeutic agent but can cause acute renal injury. Part of this acute renal injury is mediated through tumor necrosis factor-α (TNF-α). Cisplatin activates p38 MAPK and induces apoptosis in cancer cells. p38 MAPK activation leads to increased production of TNF-α in ischemic injury and in macrophages. In vitro, cisplatin caused a dose dependent activation of p38 MAPK in proximal tubule cells. Inhibition of p38 MAPK activation led to inhibition of TNF-α production. In vivo, mice treated with a single dose of cisplatin developed severe renal dysfunction, which was accompanied by an increase in kidney p38 MAPK activity and an increase in infiltrating leukocytes. However, animals treated with a p38 MAPK inhibitor SKF86002 along with cisplatin showed less renal dysfunction, less severe histologic damage and fewer leukocytes compared with cisplatin+vehicle treated animals. The compounds and methods described herein are useful for preventing acute renal injury.

Periodontitis.

The proinflammatory mediator bradykinin (BK) stimulates interleukin-8 (IL-8) production in human gingival fibroblasts in vitro and plays an important role in the pathogenesis of various inflammatory diseases including periodontitis. The specific p38 mitogen-activated protein kinase (MAPK) inhibitor SB 203580 reduced IL-8 production stimulated by the combination of BK and IL-1β as well as the IL-1β-stimulated IL-8 production. The compounds and methods described herein are useful for treating or preventing periodontitis.

Pharmaceutical Compositions

While it is possible for the compounds described herein to be administered alone, it may be preferable to formulate the compounds as pharmaceutical compositions. As such, in yet another aspect, pharmaceutical compositions useful in the methods of the invention are provided. More particularly, the pharmaceutical compositions described herein may be useful, inter alia, for treating or preventing inflammatory conditions, e.g., conditions associated with p38 activity or cytokine activity or any combination thereof. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. A preferred subject is a mammal. A mammal includes any mammal, such as by way of non-limiting example, cattle, pigs, sheep, goats, horses, camels, buffalo, cats, dogs, rats, mice, and humans. A highly preferred subject mammal is a human.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds described herein may be formulated for oral administration in a lipid-based formulation suitable for low solubility compounds. Lipid-based formulations can generally enhance the oral bioavailability of such compounds.

As such, a preferred pharmaceutical composition comprises a therapeutically or prophylactically effective amount of a compound described herein, together with at least one pharmaceutically acceptable excipient selected from the group consisting of—medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of $\alpha$-, $\beta$-, and $\gamma$-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

A pharmaceutical composition contains a total amount of the active ingredient(s) sufficient to achieve an intended therapeutic effect. More specifically, in some embodiments, the pharmaceutical composition contains a therapeutically effective amount (e.g., an amount of an SAPK-modulating compound that is effective in the prevention or treatment of the symptoms of an inflammatory disease or condition, wherein the compound exhibits an $EC_{50}$ in the range of about 1 µM to about 1000 µM, preferably about 50 µM to about 650 µM, for inhibition of at least one p38 MAPK). The total amounts of the compound that may be combined with the carrier materials to produce a unitary dosing form will vary depending upon the host treated and the particular mode of administration. Preferably, the compositions are formulated so that a dose of between 0.01 to 100 mg/kg body weight/day of an SAPK-modulating compound is administered to a patient receiving the compositions.

Example 1

Compounds are screened for the ability to inhibit ATF2 phosphorylation by p38 MAP kinase in vitro. The ability of compounds to inhibit ATF2 phosphorylation in this in vitro assay is correlated with the inhibition of p38 MAP kinase and TNFα expression in vivo, and is therefore an indicator of potential in vivo therapeutic activity (Raingeaud, J. et al. 1995 *J. Biol. Chem.* 270:7420-7426; Brinkman, M. N., et al. 1999 *J. Biol. Chem.* 274:30882-30886; and Fuchs, S. Y. et al. *J. Biol. Chem.* 275:12560-12564, 2000).

All kinases and the substrate ATF2 are acquired from Upstate (Charlottesville, Va.). p38 MAP Kinases are recombinant human full-length proteins with an amino-terminal GST fusion, expressed in and purified from *E. coli*. ATF2 is a GST fusion protein containing amino acids 19-96 of human ATF2 expressed in *E. coli*. All proteins are aliquoted and stored at −80° C.

p38 MAP kinase assays are performed using an assay buffer containing 25 mM HEPES, pH 7.5, 10 mM $MgCl_2$, 2 mM DTT, 20 mM β-glycerophosphate, 0.1 mM $Na_3VO_4$, 40 µM ATP and 1.25 µM of ATF2, together with 6 ng of p38α protein, 12 ng p38β protein, 1.5 ng p38γ, or 0.4 ng JNK2α2. Compounds are serially diluted in DMSO and 2 µL of test compound at various concentrations is used. The vehicle control receives DMSO only.

Test compounds are pre-incubated with 20 µl of enzyme in kinase buffer (25 mM HEPES, pH 7.5, 10 mM $MgCl_2$, 2 mM DTT, 20 mM β-glycerophosphate and 0.1 mM $Na_3VO_4$) at room temperature for 15 minutes. Reactions are initiated by addition of 30 µl substrate solution to yield a final concentration of 40 µM ATP and 1.25 µM ATF2 in kinase buffer. The reactions are incubated for 30 minutes at 37° C. and terminated by the addition of 18 µl of 200 mM EDTA. An ELISA method is used to measure the phosphorylation of ATF2 at Thr 69. High binding 96-well plates are coated with 50 µl of kinase reaction for 1 hour at 37° C. The coated plates are washed with 200 µl washing buffer (25 mM Tris HCl, pH 8.3, 192 mM glycine, 0.1% SDS and 0.05% Tween-20) three times. The plates are then washed three times with SuperBlock in TBS (Pierce, 37535). After blocking, plates are incubated with 50 µl of rabbit anti-phospho-ATF2 antibody (Cell Signaling, 9221L, 1:500) for 30 minutes at 37° C.

Plates are washed three times with washing buffer prior to incubation with 50 HRP-conjugated goat anti-rabbit antibody (Cell Signaling, 7074, 1:500) for 30 minutes at 37° C. Plates are then washed three times with washing buffer before incubation with 50 µl of Ultra TMB-ELISA (Pierce, 34028) for 8 minutes at room temperature. Finally, 50 µl of phosphoric acid (1 M) is added to stop reactions and plate absorbance is read at 450 nm on a SpectraMax 250 plate reader.

The compounds inhibit the phosphorylation of ATF2 in this in vitro assay. Preferred compounds exhibit $EC_{50}$ values of between about 1 µM and about 1000 µM, preferably about 50 µM to about 650 µM.

Example 2

Compounds are screened for the ability to inhibit TNFα release from THP-1 cells stimulated with lipopolysaccharide (LPS) in vitro. The ability of compounds to inhibit TNFα release in this in vitro assay is correlated with the inhibition of p38 activity and TNFα, and is therefore an indicator of potential in vivo therapeutic activity (Lee J. C. et al. 1993 *Ann. N.Y. Acad. Sci.* 696:149-170; and 1994 *Nature* 372: 739-746).

THP-I cells from ATCC (TIB202) are maintained at 37° C., 5% $CO_2$ in RPMI 1640 media (MediaTech, Herndon, Va.) containing 4.5 g/L glucose, supplemented with 10% fetal bovine serum, 1% penicillin/streptomycin and 50 µM β-mercaptoethanol.

Test compounds are initially dissolved in RPMI media with 1% DMSO (v/v). Compounds are then serially diluted in RPMI media for all subsequent dilutions. The assay is performed under sterile conditions. THP-1 cells at a culture density of 6-8×10⁵ cells/ml are collected and resuspended in the RPMI media at 10⁶ cells/ml. 100 µl of resuspended cells are added to each well, which contain 100 µl of a test compound. Test compounds are prepared at twice the final concentration. Final DMSO concentration is no more than 0.5% (v/v). Cells are preincubated with compound for 60 minutes at 37° C., 5% $CO_2$ prior to stimulation with lipopolysaccharide (LPS) (Sigma L-2880, 4 mg/ml stock in PBS). The final LPS concentration in each well is 10 or 30 µg/ml for TNFα and IL-1β release, respectively. Unstimulated control cell suspensions receive PBS vehicle only. Cell mixtures are incubated for 18 or 48 hours for TNFα and IL-1β release, respectively. 150 µl of supernatants are taken and transferred to a fresh plate and stored at −20° C. until farther analysis. TNFα and IL-1β levels are measured using ELISA kits. A Luminescence is used as the plate reader. Analysis is performed by non-linear regression to generate a dose response curve. The calculated $EC_{50}$ value is the concentration of the test compound that causes a 50% decrease in TNFα or IL-1β levels.

Compounds inhibit the release of TNFα, IL-1β or both TNFα, and IL-1β in this in vitro assay. Preferred compounds exhibit $EC_{50}$ values for TNFα and/or IL-1β of between about 1 µM and about 1000 µM, preferably about 50 µM to about 650 µM. Data are provided in Table 2 below.

TABLE 2

| No.[1] | $X_3$ | $R_2$ | $R_4$ | Z | TNF EC$_{50}$ (µM)[2] | Toxicity[3] |
|---|---|---|---|---|---|---|
| 13 | —H | —CH$_3$ | —H | O | A | ≥1 mM |
| 7 | —H | —H | —H | O | B | D |
| 9 | —OH | —H | —H | O | C | D |
| 11 | —F | —H | —H | O | B | D |
| 8 | —H | —CF$_3$ | —H | O | B | D |
| 12 | —F | —CF$_3$ | —H | O | C | D |
| 5 | —OH | —CH$_3$ | —H | O | A | ≥1 mM |
| 1 | —H | —CH$_2$OH | —H | O | B | D |
| 2 | —H | —COOH | —H | O | C | D |
| 3 | —H | -glucuronide | —H | O | C | D |
| 6 | —H | —CH$_2$OCH$_3$ | —H | O | A | ≥1 mM |
| 4 | —H | —CH$_3$ | —OH | O | A | ≥1 mM |
| 14 | —F | —CH$_3$ | —H | O | B | D |
| 15 | —OCH$_3$ | —CF$_3$ | —H | O | C | D |
| 16 | —COCH$_3$ | —H | —H | O | C | D |
| 10 | —OH | —CF$_3$ | —H | O | A | D |
| 17 | —H | -phenyl | —H | O | C | D |
| 18 | —H | —CH$_3$ | —H | S | C | D |
| 25 | See note 4 | CH$_3$ | —H | O | B | B |
| 26 | —H | —Br | —H | O | A | B |
| 27 | —OCH$_3$ | —Br | —H | O | A | A |
| 28 | —OH | —CH$_2$F | —H | O | C | D |
| 29 | —OH | —CHF$_2$ | —H | O | C | D |
| 30 | —OH | —Br | —H | O | A | A |
| 31 | —OCH$_3$ | —CH$_2$F | —H | O | A | A |
| 32 | —OCH$_3$ | —CHF$_2$ | —H | O | A | A |
| 33 | —H | See note 5 | —H | O | C | D |
| 24 | —H | CO$_2$CH$_3$ | —H | O | C | D |

[1] Compound number as shown in Table 1
[2] A: ≤2,000; B: >2,000; C: Inconclusive (e.g., no data or no activity observed)
[3] D: Inconclusive (e.g., no data or no toxicity observed)
4 Compound 25 is as depicted in Table 1, namely the aryl group attached to a 2-pyridone nitrogen is an N-methylpyridinium moiety
5 Compound 33 is as depicted in Table 1, namely a bromoaryl group fused to the 5 and 6 positions of a 2-pyridone ring

Example 3

Compounds are screened for the ability to inhibit TNFα release from primary human peripheral blood mononuclear cells (PBMC) stimulated with lipopolysaccharide (LPS) in vitro. The ability of compounds to inhibit TNFα release in this in vitro assay is correlated with the inhibition of p38 activity and is therefore an indicator of potential in vivo therapeutic activity (2002 *Osteoarthritis & Cartilage* 10:961-967; and Laufer, S. A. and Wagner, G. K. 2002 *J. Med. Chem.* 45: 2733-2740).

Human peripheral blood mononuclear cells (PBMC) are isolated by differential centrifugation through a Ficoll-Hy-Paque density gradient from pooled serum of 3-8 individual blood donors. Isolated PBMC contain approximately 10% CD-14 positive monocytes, 90% lymphocytes and <1% granulocytes and platelets. PBMC (10$^6$/ml) are cultured in polystyrene plates and stimulated with lipopolysaccharide (LPS; 50 ng/ml; Sigma, St. Louis, Mo.) in the presence and absence of the test compound in serial dilutions, in duplicate, for 24 hr at 37° C. in GIBCO™ RPM1 medium (Invitrogen, Carlsbad, Calif.) without serum. The TNFα level in cell supernatants is determined by ELISA using a commercially available kit (MDS Panlabs #309700).

Preferred compounds inhibit the release of TNFα in this assay with an EC$_{50}$ value of between about 1 µM and about 1000 µM, preferably about 50 µM to about 650 µM.

Example 4

Compounds are screened for the ability to inhibit the release of TNFα in an in vivo animal model (See, e.g., Griswold D. E. et al. 1993 *Drugs Exp. Clin. Res.* 19:243-248; Badger, A. M. et al. 1996 *J. Pharmacol. Exp. Ther.* 279:1453-1461; Dong, C. et al. 2002 *Annu. Rev. Immunol.* 20:55-72 (and references cited therein); Ono, K. and Han, J. 2000 *Cellular Signalling* 12:1-13 (and references cited therein); and Griffiths, J. B. et al. 1999 *Curr. Rheumatol. Rep.* 1:139-148).

Without being bound by any particular theory, it is believed that inhibition of TNFα in this model is due to inhibition of p38 MAP kinase by the compound.

Male Sprague-Dawley rats (0.2-0.35 kg) are randomly divided into groups of six or more and are dosed intravenously by infusion or bolus injection, or are dosed orally with test compounds in a suitable formulation in each case. Thirty minutes following end of infusion or bolus injection, and 1-2 hr following oral administration, lipopolysaccharide *E. coli*/0127:B8 (0.8 mg/kg) is administered IV. Blood samples are collected 1.5 hours post-treatment with LPS. Serum TNFα☐ levels are determined using the ELISA kit from Biosource (KRC3011C) and compared to that from vehicle-treated control.

Preferred compounds inhibit the release of TNFα in this in vivo assay. Preferred compounds exhibit an ED$_{50}$ value of less than 500 mg/kg, preferably less than 400 mg/kg, preferably less than 200 mg/kg, preferably less than 100 mg/kg, more preferably, less than 50 mg/kg, more preferably, less than 40 mg/kg, more preferably, less than 30 mg/kg, more preferably, less than 20 mg/kg, more preferably, less than 10 mg/kg.

The methods of determining the EC$_{50}$ of the inhibition of p38 by a compound include any methods known in the art that allow the quantitative detection of any of the downstream substrates of p38 MAPK as described above. Therefore, these methods additionally include but limited to detection of expression of genes known to be regulated by p38 either individually, or by gene arrays.

Example 5

The following methods can be used for (1) a kinase assay for determination of EC$_{50}$, (2) a non-radiomentric kinase assay for determination of EC$_{50}$, (3) modulation of induction of TNFα expression, (4) a test for cell toxicity, and (5) an assay to test the effect of compounds on collagen production.

Kinase Assay

The activity of the P38 kinase isoforms P38γ and P38α is determined by phosphorylation of ATF-2 in presence of $^{32}$P-γ-ATP. The incorporation of $^{32}$P into ATF-2 in the presence or absence of inhibitors is determined. Pirfenidone and its different derivatives are tested for inhibition of P38γ and P38α kinase activity in this biochemical assay. The compounds are solubilized in water or DMSO and tested at different concentrations from 0 to10 mM using the appropriate solvent for dilutions and as vehicle control. The enzymes P38γ and P38α are obtained as activated and purified recombinant protein (Upstate, Charlottesville, Va.). The activated enzyme is used at 24.8 nM in the final reaction. The enzymes are diluted prior to the reaction in the following buffer (1M HEPES, pH 7.4, 500 mM DTT, 1%

Triton X-100 and 10 mg/ml BSA). The reaction is performed in the following solution that is prepared as a two fold stock solution (1M HEPES, pH 7.4, 500 mM DTT and 1% Triton X-100) and non-radioactive ATP is present in the reaction at 6.25 μM ATP (Cell Signaling, Beverly, Mass.). To determine the phosphorylation of ATF-2, γ-[$^{32}$P]-ATP 3000 Ci/mmol is added to each reaction at a concentration of 7.5 μM. ATF-2 (Cell Signaling, Beverly, Mass.) as a kinase substrate is used at 3 μM. As a first step in assembling the enzyme reaction, activated kinase and inhibitor or the appropriate vehicle control are added to reaction buffer and incubated for 30 min at room temperature. The kinase reaction is initiated by the addition of ATF-2 and ATP mixture. The final volume for each reaction is 20 μl and performed at room temperature for 30 minutes. After the 30 minutes of incubation 80 ul of Laemmlie buffer is added. Subsequently 20% of the reaction is separated by SDS-Page (BioRad, Hercules, Calif.) under reducing conditions. After electrophoresis, the gel is exposed to a phosphorimager plate and analyzed using a phoshoimager (Storm System, Amersham Biosciences, Piscataway, N.J.). The signal obtained is quantified after background correction and calculated as percent inhibition using the uninhibited kinase activity with the vehicle control as 0% inhibition. The kinase activity, in the presence of different inhibitor concentrations, is plotted using Kaleidagraph (Synergy Software, Reading, Pa.) to determine the $EC_{50}$ for each compound and tested P38 kinase.

Non-Radiometric Kinase Assay

An alternate, non-radiometric kinase assay was also employed to define the EC50 for inhibition of P38. In this assay, p38 kinase transfers a phosphate from ATP to an EGF-R peptide substrate, resulting in the formation of phosphorylated EGF-R peptide with the concomitant conversion of ATP to ADP. In an uncoupled reaction, p38 also hydrolyzes ATP at a slower rate in the absence of peptide substrate (Fox et al, FEBS Lett 1999), which contributes slightly to ATP consumption. Thus, the amount of ATP consumed is directly proportional to p38 activity. At the end of a kinase reaction, the amount of ATP remaining is determined using Kinase-Glo Plus Luminescent Kinase Assay (Promega, Inc., Madison, Wis.). These reagents use residual ATP to support the ATP-dependent enzymatic conversion of beetle luciferin to oxyluciferin with the concomitant production of light, which is detected by a luminometer.

Kinase reactions are conducted by mixing compound (diluted in DMSO and assay buffer) with either p38α or p38γ, and EGF-R peptide substrate (AnaSpec, Inc., San Jose, Calif.) in assay buffer. Reactions are then initiated by the addition of ATP and allowed to run for 45 minutes at room temperature. Final buffer conditions are: 20 mM HEPES (pH 7.4), 2 mM DTT, 0.1% Triton-X-100, 10 mM $MgCl_2$, 10% glycerol, 12.5 mM p38α or p38γ (Upstate, Charlottesville, Va.), 50 μM EGF-R peptide substrate, and 10 μM ATP. The final assay volume is 10 μL. A control reaction is performed in the absence of compound. Additional control reactions that omit p38 are performed at every compound concentration. All reactions are performed in triplicate.

Forty-five minutes after initiation of the kinase reaction, the reaction is quenched by the addition of 10 μL of Kinase-Glo Plus assay reagent. The luciferase reaction is allowed to equilibrate for 15 minutes prior to being read on an Envision Multilabel Plate Reader (Perkin Elmer Life and Analytical Sciences, Boston, Mass.). Data are plotted as luminescent signal versus log compound concentration in KaleidaGraph (Synergy Software, Reading, Pa.). $EC_{50}$ values are determined by fitting the data to 4-parameter binding equation using a fixed upper bound that is determined from control reactions in the absence of p38 (as luminescence is inversely related to kinase activity).

Inhibition of TNFα Induction

THP-1 (ATCC, Rockville, Md.) is grown under regular tissue culture conditions as recommended by ATCC. 18 hours prior to the experiment, cells were plated in a 96 well format in regular culture media containing 1% serum and 0.25 ml culture volume at a density of 500,000 cells per well. The compound is added to each well in triplicates and the appropriate solvent control is included in each assay. The p38 inhibitor SB203850 at 1 μM/ml (Upstate, Waltham, Mass.) is included as a positive control in each assay. For the induction of TNFα expression, 1 μg/ml LPS is added to each well 30 minutes post compound addition. Following a 4 hour incubation under tissue culture conditions the cells are sedimented by centrifugation (10 min, 1000 rpm, Beckman table top centrifuge) and a fraction of the cell free supernatant is collected and used in a tenfold dilution for the quantification in the TNFα specific ELISA (R&D Systems, Minneapolis, Minn.). The TNFα ELISA is performed according to the directions provided by the manufacturer. The TNFα is detected in pg/ml and plotted as fractional activity normalized to the TNFα expression in the solvent control.

Compound Toxicity Testing in a Cell Based Assay

The release of LDH as result of a disrupted cell membrane is applied as a measure of cell toxicity. LDH is detected by its enzymatic activity using a commercially available diagnostic kit (Roche Diagnostics, Cat #1 644 793). THP-1 cells are used for determination of cell toxicity for consistency with the induced TNFα expression in the previous experiment. As previously described for testing of inhibition of TNFα induction, cells are cultured in a 96 well format under 1% serum and regular tissue culture conditions. The compounds are added at different concentrations in triplicate. The appropriate solvent control is used in each assay. After compound addition the cells are cultured 18 hours under regular tissue culture conditions. After this incubation period, the positive control is initiated by adding Triton-X-100 (2% v/v) to untreated cells and incubated for an additional 10 minutes for complete cell lysis. Subsequently the cells are sedimented by centrifugation and a fraction of the supernatant removed and analyzed for LDH enzyme activity according to the manufacturer's instructions. The data is typically reported as % cell toxicity normalized to the Triton-X-100 lysed cells as 100% cell toxicity.

Toxicity data are also obtained using a commercially available ATP assay (Molecular Probes' ATP Determination Kit A22066, available from Invitrogen) and/or using a MTT assay. Both the ATP and the MTT assays measure metabolic competence of the cell. The MTT assay measures the ability of the cell to reduce a marker substrate, which is related to metabolic competence (i.e. viability). The ATP assay measures the cellular ATP concentration in the presence and absence of compound. Toxic compounds lead to reduced metabolic activity which leads to a reduction in ATP concentration.

Assay for Effect of Compounds on Collagen Production

HFL-1 Cells (ATCC, Rockville, Md.) were grown under regular tissue culture conditions in complete media containing 10% fetal bovine serum (FBS; Mediatech, Inc., Herndon, Va.). Cells in early passage were plated in 6 well plates. When the cells reached confluence, the media was removed, cells washed with PBS, and the cells were kept overnight in complete media containing 0.1% FBS. The media was then replaced with fresh media plus 0.1% FCS, 10 μM L-Proline (EMD Chemicals, Gibbstown, N.J.), 20 μg/mL ascorbic acid (EMD Chemicals, Gibbstown, N.J.). Compounds were added to triplicate wells to a final concentration of 1 mM from 100× stock solutions in DMSO. One hour after the addition of compound, the cells were treated with TGF-β1 (Sigma-Aldrich, St. Louis, Mo.) to a final concentration of 10 ng/mL (25 ng total). Three days after addition of TGF-β, the media was removed, cells were washed with PBS and then lysed. The total collagen content of lysed cells was assessed with a dye-based collagen assay (Sircol Collagen Assay, Newtownabbey, Northern Ireland) and a μQuant plate-based spectrophotometer (BioTek Insturments, Inc., Winooski, Vt.) with appropriate standard curves. The dynamic range of the assay is defined by cells that were mock treated (1% DMSO without compound) in the presence and absence of TGF-β. Data are reported in Table 3 as the percent inhibition of TGF-β-induced collagen as determined in the following equation:

% inhibition=100*[(collagen,mock/+TGF-β)−(collagen,treated/+TGF-β)]/[(collagen,mock/+TGF-β)−(collagen,mock/-TGF-β)]

TABLE 3

| Compound No. | % Inhibition of TGF-β Stimulated Collagen Synthesis |
|---|---|
| 8 | 48 |
| 14 | 23 |
| 15 | 49 |
| 26 | 58 |
| 30 | 69 |

Example 6

Preparation of 1-(4-hydroxyphenyl)-5-(trifloromethyl)-2-pyridone (Compound 10): A mixture of 5-(trifloromethyl)-2(1H)-pyridone (815.5 mg, 5 mmol), 4-iodoanisole (2.34 g, 10 mmol), CuI (952 mg, 5 mmol), $K_2CO_3$ (691 mg, 5 mmol) and DMF (5 ml) was heated at 135° C. overnight. The reaction mixture was diluted with 10% ammonia (15 ml) and extracted with ethyl acetate. The organic extract was washed with saturated sodium chloride, dried over magnesium sulfate and evaporated. Column chromatography purification (30% ethyl acetate-hexane) afforded 526 mg (39.2%) of 1-(4-methoxyphenyl)-5-(trifloromethyl)-2-pyridone. This compound (268.2 mg, 1 mmol) was treated with 1M $BBr_3$ solution in dichloromethane (DCM, 2 ml) in DCM (5 ml) for 2 hours at 0° C. Reaction mixture was diluted with DCM and washed 3 times with water. Organic phase was dried over sodium sulfate and evaporated. The residue was separated by column chromatography (20% ethyl acetate-DCM) to afford the title compound as a off-white solid, 226 mg (89%). The $^1$H NMR spectra was consistent with the structure of Compound 10.

Example 7

Preparation of 1-phenyl-5-acetyl-2-pyridone (Compound 16): 2-methoxy-5-acetyl pyridine (1.51 g, 10 mmol) was treated with 6N HCl at 100° C. for 5 hours. The reaction mixture was neutralized with sodium hydroxide to pH 7 and then extracted several times with DCM. Organic layer was dried over sodium sulfate, evaporated and the residue was crystallized from ethyl acetate to give 5-acetyl-2(1H)-pyridone as a white solid, 1.06 g (78%). This compound (685.7 mg, 5 mmol) was reacted with iodobenzene (0.84 ml, 7.5 mmol) in the presence of CuI (95 mg, 0.5 mmol) and $K_2CO_3$ (691 mg, 5 mmol) in DMF (5 ml) at 135° C. overnight. The reaction mixture was diluted with 10% ammonia (15 ml) and extracted with ethyl acetate. The organic extract was washed with saturated sodium chloride, dried over magnesium sulfate and evaporated. Column chromatography (10% ethyl acetate-DCM) afforded 407 mg (38%) of the target compound as a white solid. The $^1$H NMR spectra was consistent with the structure of Compound 16.

Example 8

Preparation of 1-(4-pyridinyl)-5-methyl-2-pyridone (Compound 22): Compound 22 was synthesized by condensation of 5-methyl-2(1H)-pyridone (327.4 mg, 3 mmol) with 4-bromopyridine hydrochloride (778 mg, 4 mmol) in the presence of CuI (60 mg, 0.3 mmol) and $K_2CO_3$ (1.36 g, 10 mmol) in DMF (3 ml) at 135° C. overnight. The reaction mixture was diluted with 10% ammonia (15 ml) and extracted with ethyl acetate. Organic extract was washed with saturated sodium chloride, dried over magnesium sulfate and evaporated. Column chromatography (5% MeOH-DCM) afforded 197 mg (35%) of the target compound as a yellowish solid. The $^1$H NMR spectra was consistent with the structure of Compound 22.

Example 9

Preparation of 1-phenyl-5-methyl-2-pyridinethione (Compound 18): 1-phenyl-5-methyl-2-pyridinone (555.7 mg, 3 mmol) was reacted with Lawesson's reagent (606.7 mg, 1.5 mmol) in toluene (5 ml) at 90° C. Reaction mixture was evaporated and the target compound was isolated by column chromatography (20-30% ethyl acetate-hexane) followed by crystallization from methyl-tert-butyl ether. Yield 403 mg (67%), yellow solid. The $^1$H NMR spectra was consistent with the structure of Compound 18.

Example 10

Compound 33 was prepared according to the following synthetic scheme:

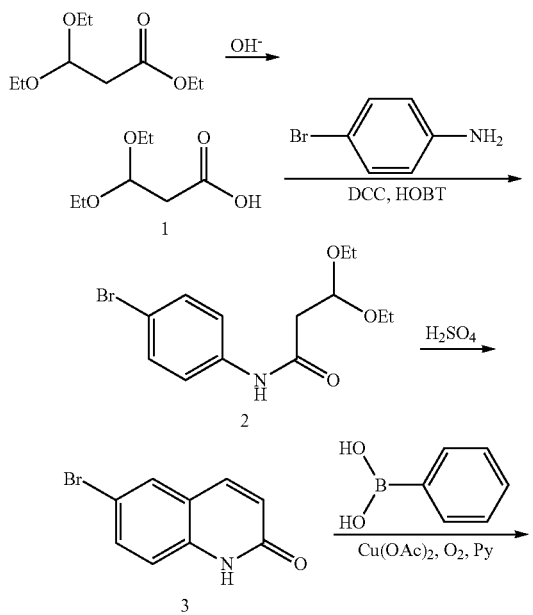

-continued

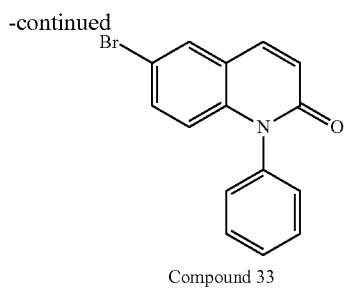

Compound 33

A mixture of commercially available ethyl 3,3-diethoxypropionate (9.7 ml, 50 mmol), sodium hydroxide (10M, 6 ml, 60 mmol) and water (15 ml) was refluxed until homogenous (approximately 30 min). After cooling to 0° C. 6N hydrochloric acid was added to bring pH of the solution to 2-3 (~10 ml). The mixture was extracted with dichloromethane, organic phase was washed with water, dried over sodium sulfate, and the solvent was removed under vacuum to give acid 1 which was used without any additional purification.

To a solution of crude acid 1 (approximately 50 mmol) in DCM (100 ml) at 0° C. was sequentially added 4-bromoaniline (10.3 g, 60 mmol), HOBT (675 mg, 5 mmol) and finally DCC (12.4 g, 60 mmol). The reaction mixture was stirred at 0° C. for 1 hour and then refluxed for another 4 hours. The solid was filtered off, filtrate was washed with saturated sodium bicarbonate, dried over sodium sulfate, and the solvent was removed under vacuum to give amide 2 as slightly yellow solid. This solid was dissolved in sulfuric acid (96%, 50 ml) at 0° C. The solution was kept at the same temperature for another 3 h and then poured into ice-water (500 ml). The solid was filtered off, washed with water, and stirred with hot acetonitrile (100 ml). Quinolinone 3 was filtered off and dried under vacuum. The yield was 10 g (91%).

Mixture of compound 3 (309 mg, 1.38 mmol), phenylboronic acid (336 mg, 2.76 mmol), Cu(OAc)$_2$ (36 mg, 0.2 mmol), molecular sieves 4a (0.3 g), pyridine (0.24 ml) and DCM (10 ml) was stirred at room temperature for 2 days. Reaction mixture was filtered trough Celite, washed with saturated sodium bicarbonate with EDTA and organic phase was dried over sodium sulfate. Compound 33 was isolated by chromatograpy (50% ethylacetate-hexane—ethylacetate). The yield was 352 mg (85%).

Example 11

The pharmacokinetic (PK) properties of pirfenidone, pirfenidone analogs and derivatives were assessed in dual canulated (right jugular/left carotid) Sprague Dawley rats (Charles River Laboratories, Inc., Wilmington, Mass.). Male rats weighing approximately 275-300 g were administered an intravenous (5 mg/Kg) or oral (50 mg/Kg via gavage) dose of compound in an appropriate formulation. Plasma samples were collected via intra-arterial canula at desired times in the 24 hours after dosing using EDTA as an anticoagulant. Three animals were used for each compound. All experiments were conducted by trained personnel in accordance with guidelines of the appropriate Institutional Animal Care and Use Committees (IACUC).

Compound concentrations were assessed by LC-MS using a MDS SCIEX API 3000 mass spectrometer (Applied Biosystems, Foster City, Calif.) coupled to a Shimadzu VP HPLC (Shimadzu Corp., Kyoto, Japan) outfitted with a Duragel G $C_{18}$ guard cartridge (Peeke Scientific, Redwood City, Calif.). Calibration samples were prepared by mixing known amounts of pirfenidone, or a pirfenidone analog or derivative, with rat plasma. A standard curve was created by serial dilution of the calibration sample in the same matrix. Both standard and analytical samples were prepared for injection to the HPLC by mixing an aliquot of plasma sample with 3 volumes of ice cold acetonitrile containing internal standard. Samples were then centrifuged. An aliquot of the resulting supernatant was then mixed with five volumes of 0.2% formic acid in water, injected to the HPLC, and resolved in a methanol gradient (containing 0.18-0.2% formic acid). The integrated analyte signal was corrected for that of the internal standard and compared to the appropriate standard curve in order to define the analyte concentration.

The pharmacokinetic parameters shown in Table 4 were derived using the WinNonlin Software package (Pharsight Corp, Mountain View, Calif.).

TABLE 4

| Route of Admin. | Dose mg/kg | Compound | $T_{1/2}$ hr. | MRTinf hr | Clobs mL/hr/kg | AUClast ng-hr/ mL × $10^6$ | E % |
|---|---|---|---|---|---|---|---|
| IV | 5 | 8 | 13.9 | 20.3 | 0.117 | 30.2 | |
| | | 19 | 2.96 | 6.26 | 0.142 | 35 | |
| | | 26 | 1.62 | 2.4 | 0.691 | 10.3 | |
| Oral | 50 | 8 | | | | 122.4 | 40.5 |
| | | 19 | | | | 191.7 | 54.8 |
| | | 26 | | | | 65.8 | 63.9 |

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference in their entirety.

What is claimed is:

1. A method of treating a p38 MAPK-mediated fibrotic condition in a subject, comprising administering to the subject a compound selected from the group consisting of:

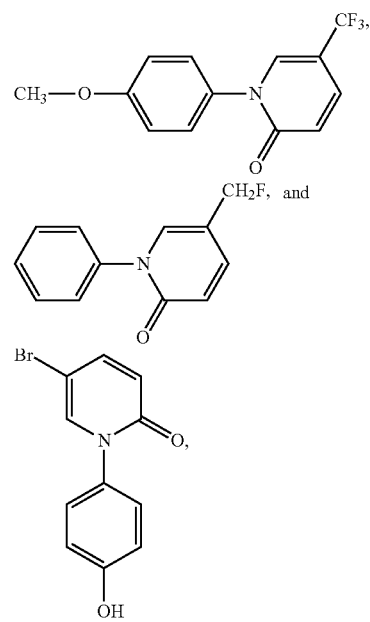

or a pharmaceutically acceptable salt thereof.

2. The method of claim 1, wherein the fibrotic condition is selected from the group consisting of pulmonary fibrosis, liver fibrosis, and renal fibrosis.

3. The method of claim 2, wherein the pulmonary fibrosis is idiopathic pulmonary fibrosis.

4. A method of inhibiting TNF-α in a cell, comprising contacting the cell with a compound selected from the group consisting of

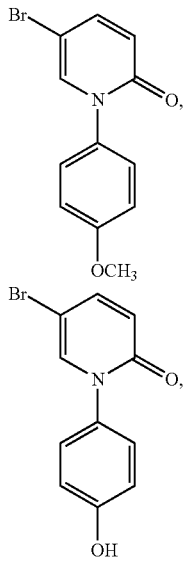

-continued

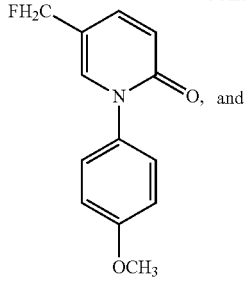

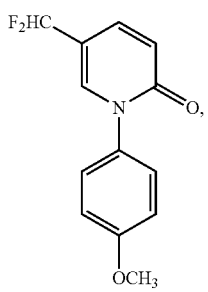

or a pharmaceutically acceptable salt thereof.

* * * * *

UNITED STATES PATENT AND TRADEMARK OFFICE
CERTIFICATE OF CORRECTION

PATENT NO. : 10,010,536 B2
APPLICATION NO. : 15/387537
DATED : July 3, 2018
INVENTOR(S) : Lawrence M. Blatt et al.

Page 1 of 1

It is certified that error appears in the above-identified patent and that said Letters Patent is hereby corrected as shown below:

On the Title Page

In Column 1, below "Related U.S. Application Data", Line 1, "(60)" should be -- (62) --.

Signed and Sealed this
Fourteenth Day of May, 2019

Andrei Iancu
*Director of the United States Patent and Trademark Office*